United States Patent [19]

Muralidhara et al.

[11] Patent Number: 4,481,224

[45] Date of Patent: Nov. 6, 1984

[54] FLAVORING WITH ALKYLTHIOALKANAL DIALKYL MERCAPTALS

[75] Inventors: Ranya Muralidhara, Fair Haven; Alan O. Pittet, Atlantic Highlands; Manfred H. Vock, Locust; David R. Bowen, Red Bank, all of N.J.

[73] Assignee: International Flavors & Fragrances Inc., New York, N.Y.

[21] Appl. No.: 521,321

[22] Filed: Aug. 8, 1983

[51] Int. Cl.³ .................. A23L 1/226; A23L 1/235
[52] U.S. Cl. .......................................... 426/535; 426/3
[58] Field of Search ........................................ 426/535

[56] References Cited

U.S. PATENT DOCUMENTS 3,863,013  1/1975  Wilson et al. ...................... 426/535
3,870,800  3/1975  Pittet et al. ........................ 426/535
4,031,257  6/1977  Wilson et al. ...................... 425/535

Primary Examiner—Joseph Golian
Attorney, Agent, or Firm—Arthur L. Liberman

[57] ABSTRACT

Described are the alkylthioalkanal dialkyl mercaptals defined according to the generic structure:

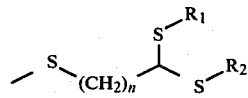

wherein n is an integer of from 1 up to 3; and wherein $R_1$ and $R_2$ are the same or different $C_1$–$C_3$ alkyl; process for preparing same and organoleptic uses thereof in augmenting or enhancing the aroma or taste of foodstuffs, chewing gums, medicinal products and toothpastes.

7 Claims, 14 Drawing Figures

GLC PROFILE FOR EXAMPLE II. CRUDE

GLC PROFILE FOR EXAMPLE I CRUDE

GLC PROFILE FOR FRACTION 1 OF EXAMPLE II.

GLC PROFILE FOR FRACTION 5 OF EXAMPLE II.

NMR SPECTRUM FOR FRACTION 5 OF EXAMPLE II.

GLC PROFILE FOR FRACTION 3 OF EXAMPLE XIII.

GLC PROFILE FOR FRACTION 3 OF EXAMPLE XIV.

NMR SPECTRUM FOR EXAMPLE XIII.

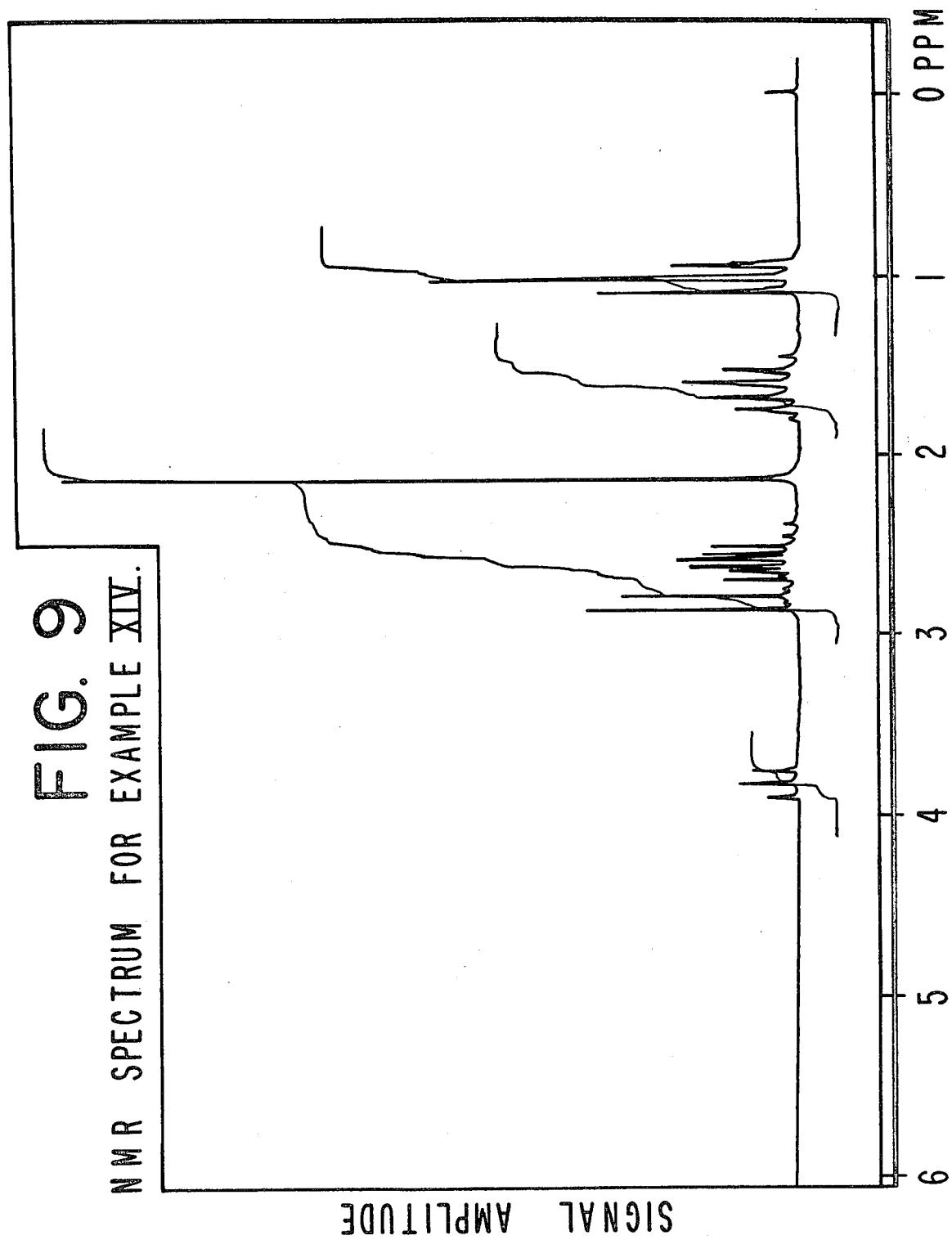

GLC PROFILE FOR EXAMPLE XVI CRUDE

GLC PROFILE FOR FRACTION 3 OF EXAMPLE XV.

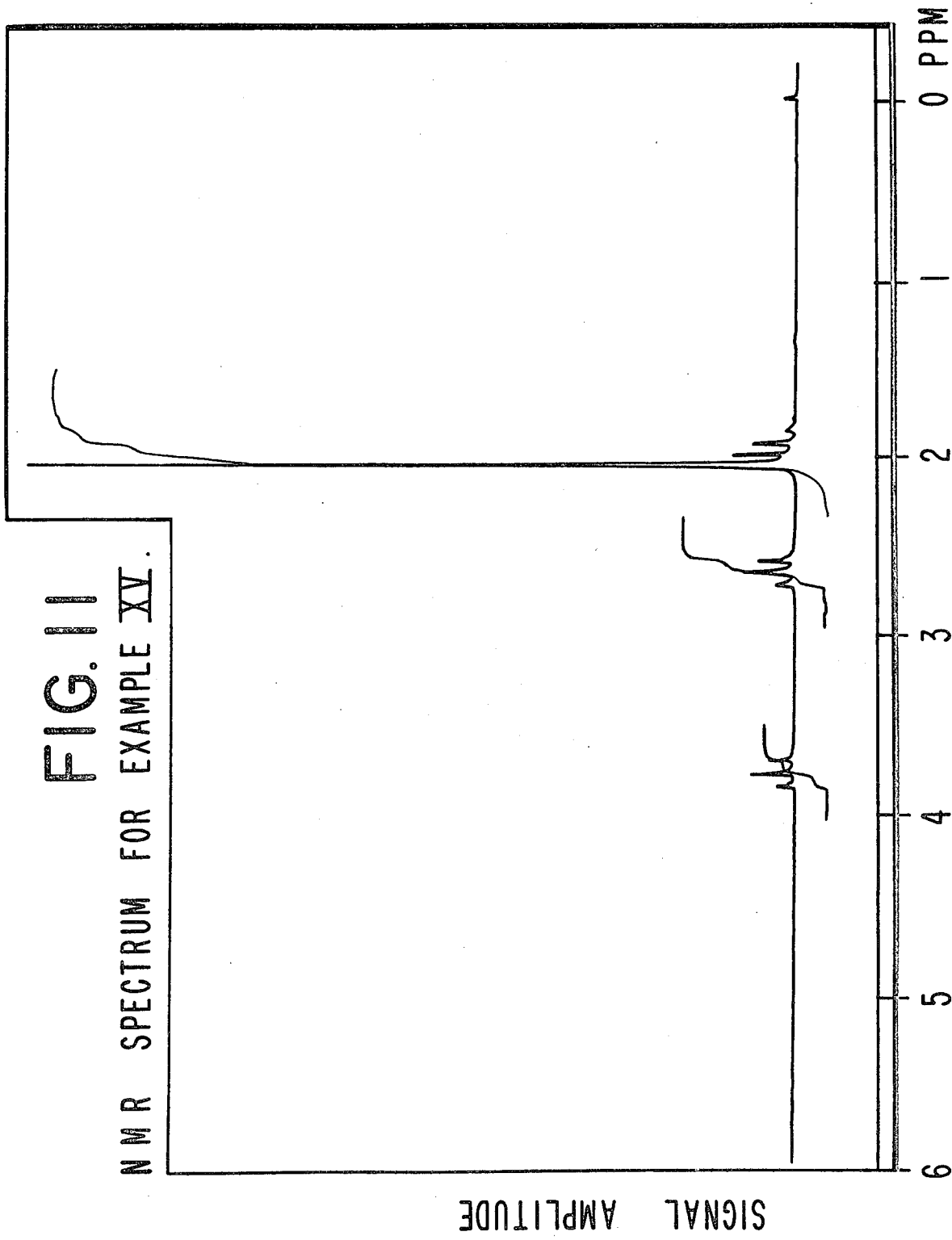
FIG. 11 NMR SPECTRUM FOR EXAMPLE XV.

GLC PROFILE FOR FRACTION 3 OF EXAMPLE XVI

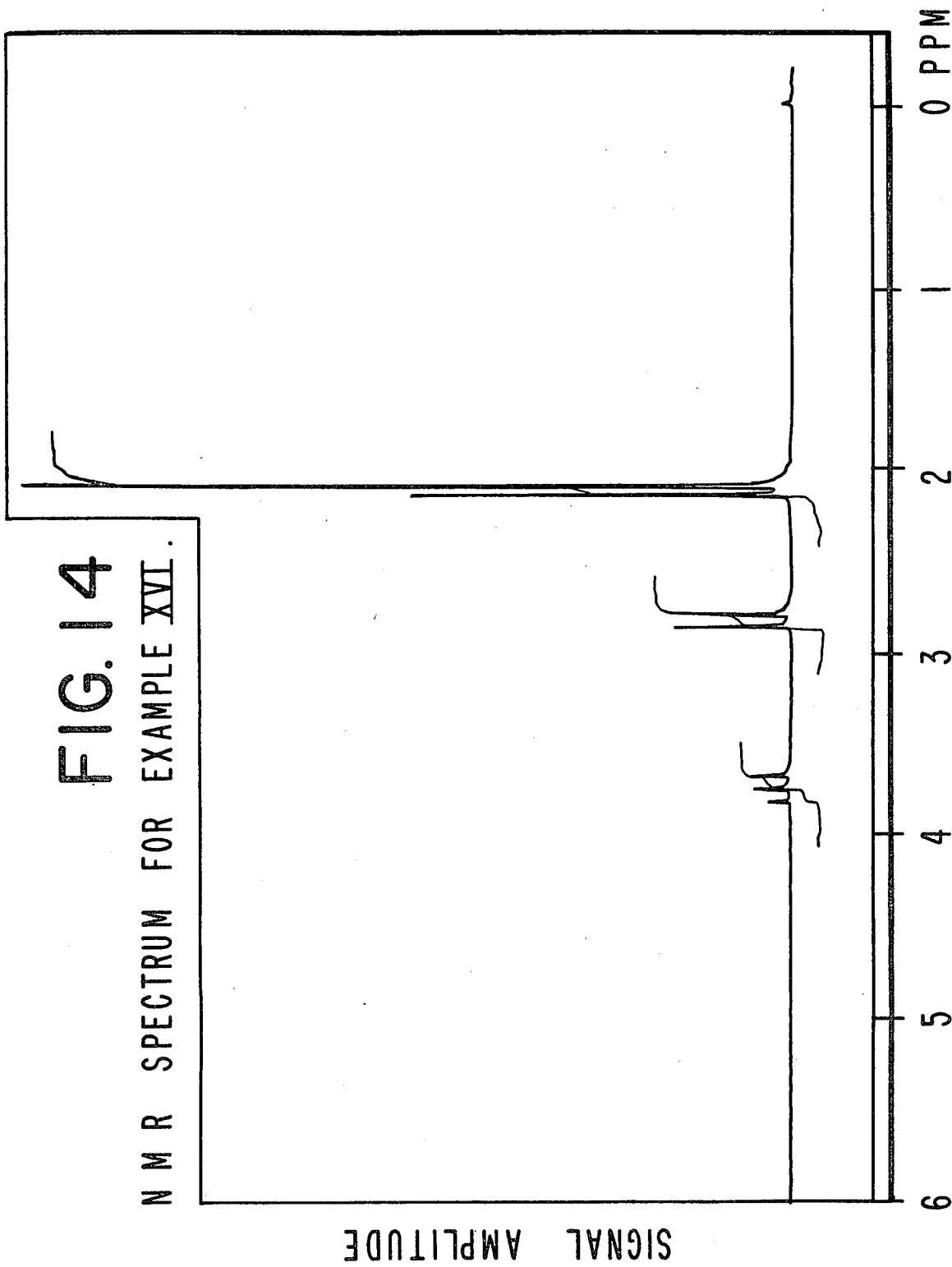

FLAVORING WITH ALKYLTHIOALKANAL DIALKYL MERCAPTALS

BACKGROUND OF THE INVENTION

The present invention relates to the novel compounds, alkylthioalkanal dialkyl mercaptals, defined according to the structure:

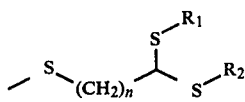

wherein n is an integer of from 1 up to 3; wherein $R_1$ and $R_2$ are the same or different $C_1$–$C_3$ alkyl and uses thereof in augmenting or enhancing the aroma or taste of consumable materials including foodstuffs, chewing gums, toothpastes and medicinal products.

Various 4-(methylthio)-butanal derivatives including 4-methylthio)-butanal itself defined according to the structure:

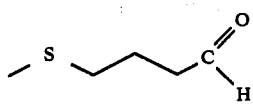

and the diethyl acetal are known for augmenting or enhancing the aroma or taste of foodstuffs and other consumable materials as is taught in U.S. Pat. No. 3,904,556 issued on Sept. 9, 1975 (the specification of which is incorporated by reference herein). Thus, the compound of 4-(methylthio)-butanal diethyl acetal is taught in said U.S. Pat. No. 3,904,556 to provide a mushroom, heated onion flavor with green, sweet tomato, oniony and garlic nuances. The 4-(methylthio)-butanal itself is taught by said U.S. Pat. No. 3,904,556 to provide a mushroom-like, tomato-like, vegetable-like, cheesy and fruity taste.

Alkanes having 3-methylthio moieties are known in the prior art, for example, that disclosed in Chem. Abstracts, Vol. 96:103327y having the structure:

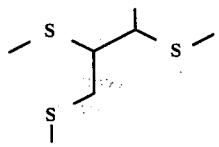

This abstract is of the Tetrahedron Letters, Vol. 22, No. 22, pages 4159–4162, 1981, (Title: "THIOSULFONIUM IONS. METHYLTHIOLATION of 3-METHYLTHIO-1-BUTENE AND CIS- AND TRANS-1-METHYLTHIO-2-BUTENE": Kim and Caserio).

U.S. Pat. No. 4,153,442 issued on May 8, 1979; U.S. Pat. No. 4,224,051 issued on Sept. 23, 1980; and U.S. Pat. No. 4,101,307 issued on June 18, 1978 each discloses plant growth regulating materials compounds defined according to the generic structure:

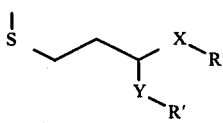

in which

X and Y, which may be the same or different, represent oxygen, sulphur or a radical N-B where B is hydrogen, a lower alkyl radical containing 1 to 4 carbon atoms, an optionally substituted aryl radical or an optionally substituted acyl radical containing from 1 to 4 carbon atoms, R and R, which may be the same or different, represent a lower alkyl radical containing from 1 to 4 carbon atoms or an acyl or amido radical containing from 1 to 4 carbon atoms; in addition, they may form with

a ring corresponding to the formula

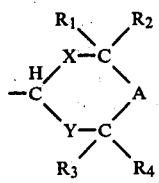

in which $R_1$, $R_2$, $R_3$ and $R_4$ which may be the same or different represent hydrogen, an alkyl radical containing from 1 to 4 carbon atoms and optionally substituted by a halogen, the radicals $NO_2$, hydroxy, alkoxy containing from 1 to 4 carbon atoms, A represents either a single bond or an alkylene chain containing from 1 to 4 carbon atoms optionally interrupted by an oxygen atom or a group N-B' where B' represents hydrogen, an optionally halogenated or hydroxylated alkyl group, an acyl group, the hydrocarbon portion of these radicals containing from 1 to 4 carbon atoms, or a cycle having in common with the preceding cycle 1 to 2 carbon atoms and containing from 3 to 6 carbon atoms, from 0 to 2 oxygen atoms and/or a group N-B, or a ring corresponding to the formula

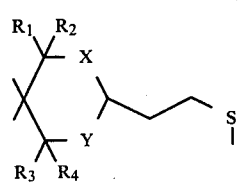

Included in this generic structure is the genus defined according to the structure:

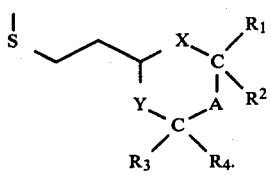

Although the generic structure set forth in the aforementioned U.S. Pat. Nos. 4,153,442, 4,224,051 and 4,101,307 contemplate within the genus a number of the compounds of the instant application, this disclosure is a "shot-gun" disclosure because it does not include the specific compounds of our invention, nor does it set forth the criticality of the compounds of our invention in their uses for their organoleptic properties.

Nagao, et al, Tetrahedron Letters No. 34, Pages 3167–3168 (1979) discloses the genus of compounds defined according to the structure:

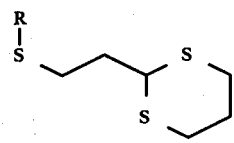

in a synthetic root to yield certain ketones. In this genus R may be methyl, ethyl, propyl, butyl, tolyl, tolyl methoxy, allyl or phenyl. This genus is not part of the instant invention. Furthermore, the Nagao, et al paper does not disclose the organoleptic uses of such compounds.

Nothing in the prior art, however, discloses the genus defined according to the structure:

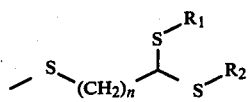

wherein n is an integer of from 1 up to 3; and wherein $R_1$ and $R_2$ are the same or different $C_1$–$C_3$ alkyl; or uses of the constituents thereof in augmenting or enhancing the aroma or taste of foodstuffs, chewing gums, toothpastes and medicinal products. Nothing in the prior art discloses the unique organoleptic properties of the compound defined according to the structure:

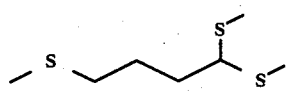

as well as any of the other members of the genus defined according to the structure:

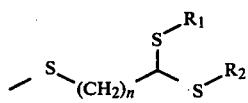

wherein n is an integer of from 1 up to 3; and wherein $R_1$ and $R_2$ are the same or different $C_1$–$C_3$ alkyl; which are unobvious and advantageous.

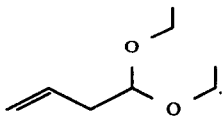

Figure 2:
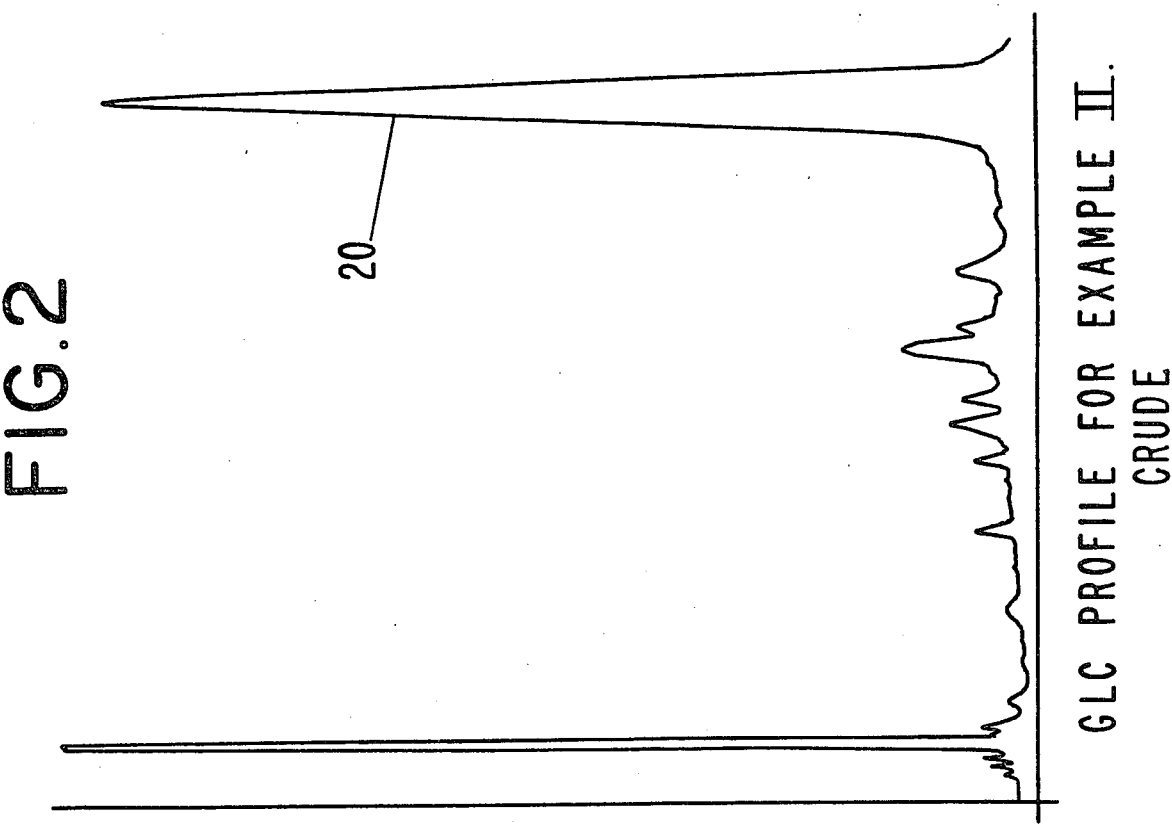

FIG. 2 is the GLC profile of the crude reaction product of Example II containing the compound having the structure:

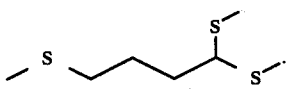

Figure 3:
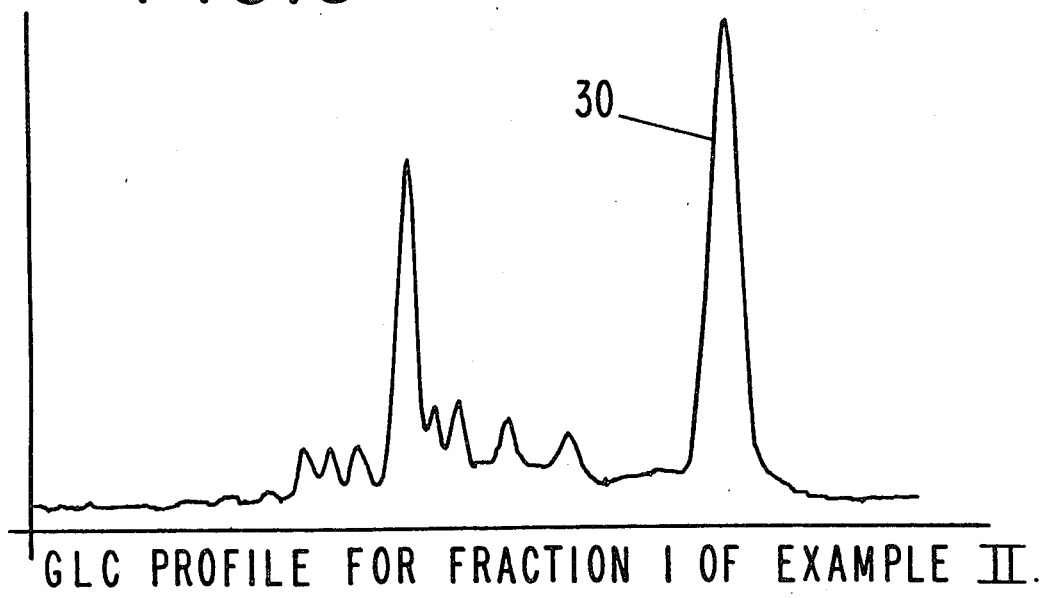

FIG. 3 is the GLC profile of Fraction 1 of the distillation product of the reaction product of Example II containing the compound having the structure:

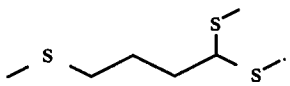

Figure 4:
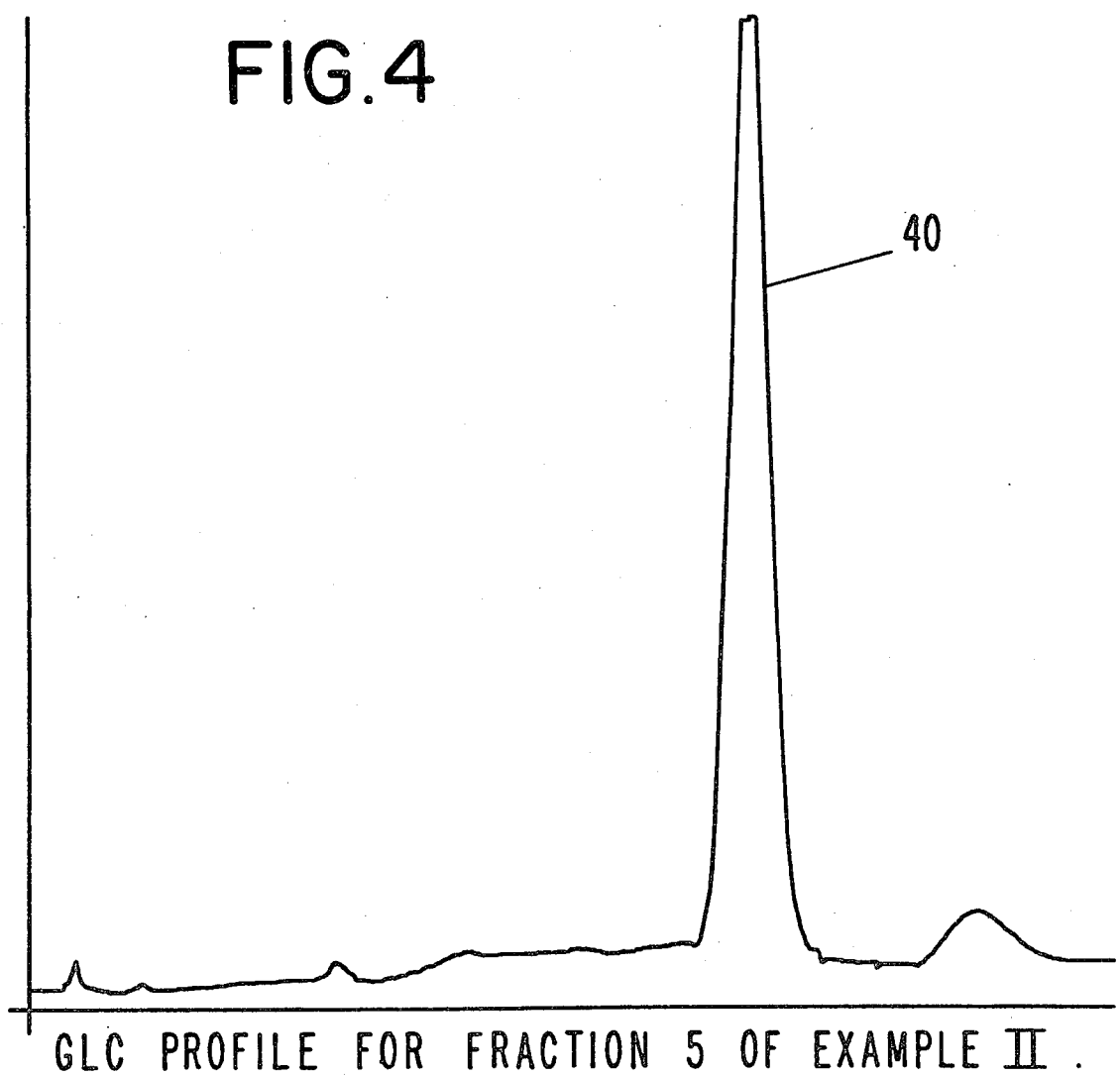

FIG. 4 is Fraction 5 of the distillation product of the reaction product of Example II containing the compound having the structure:

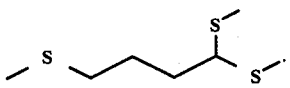

Figure 5:
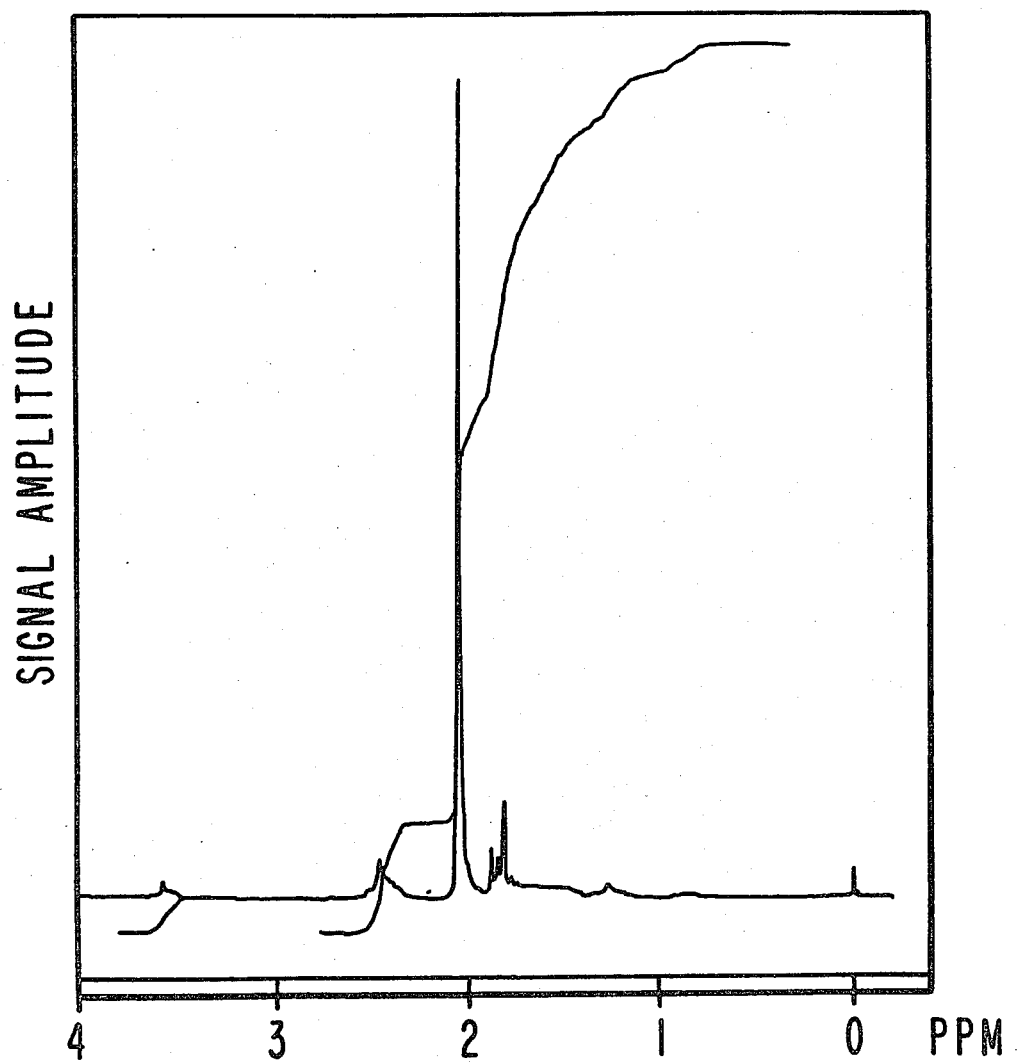

FIG. 5 is the NMR spectrum for Fraction 5 of the distillation product of the reaction product of Example II containing the compound having the structure:

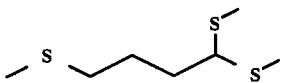

(Conditions: Field strength 100 MHz; solvent: $CFCl_3$).

Figure 6:
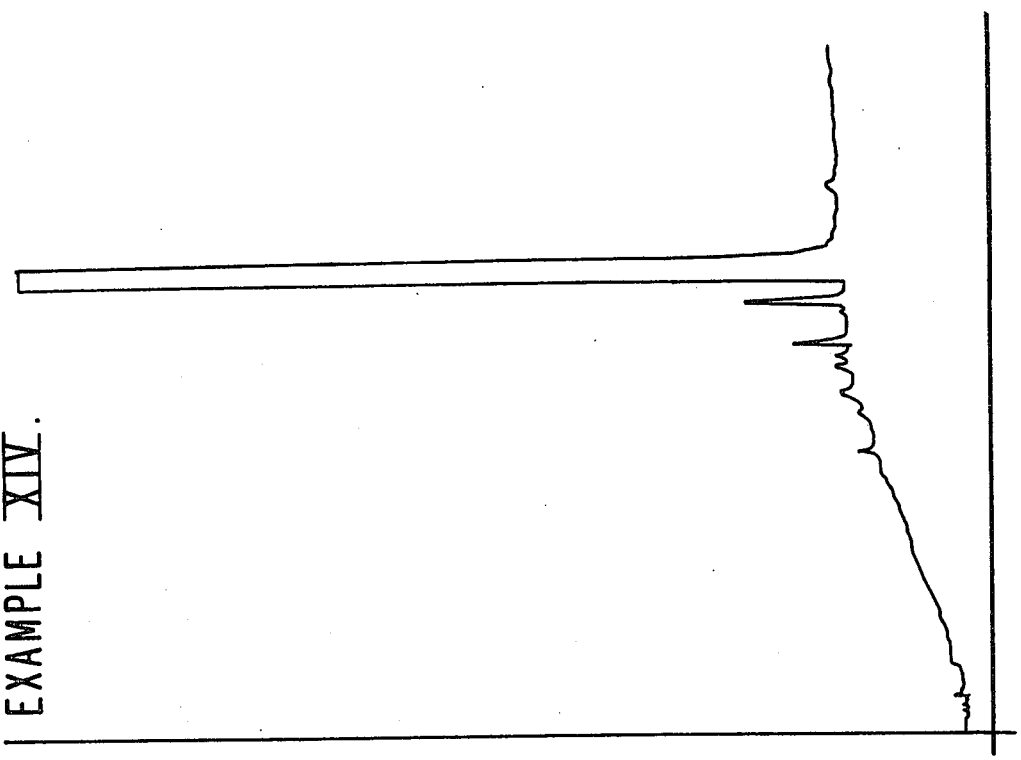

FIG. 6 is the GLC profile for Fraction 3 of the distillation product of the reaction product of Example XIII containing the compound having the structure:

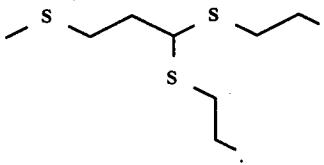

Figure 7:
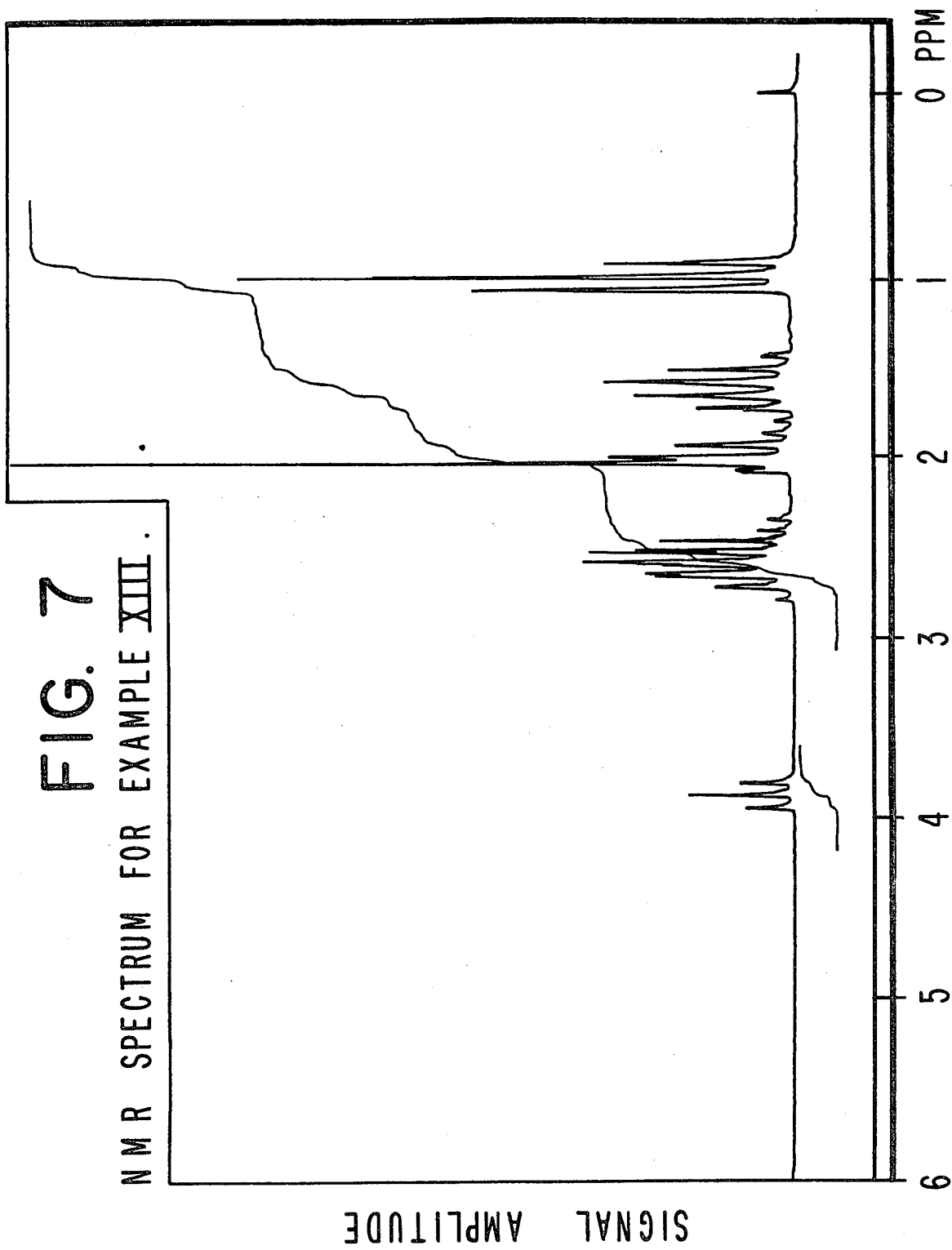

FIG. 7 is the NMR spectrum for the compound produced according to Example XIII having the structure:

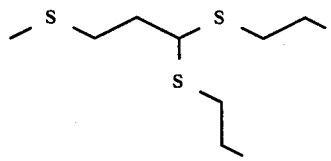

(conditions: Field strength: 100 MHz; Solvent: CFCl₃).

Figure 8:
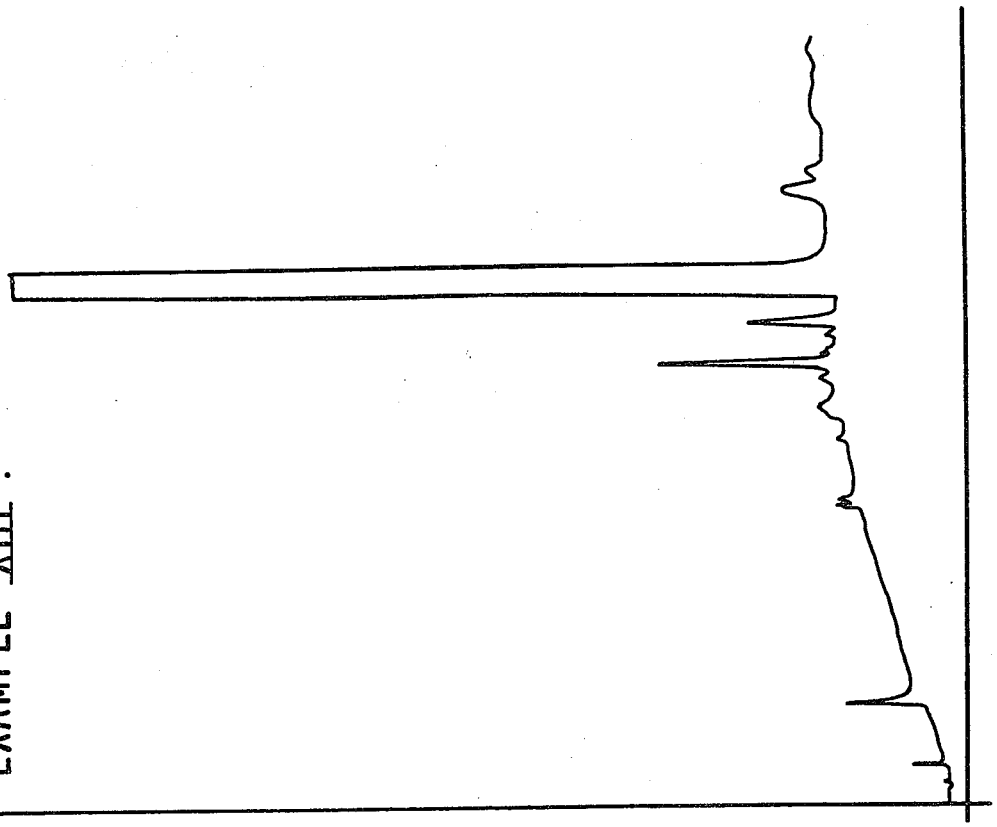

FIG. 8 is the GLC profile for Fraction 3 of the distillation product of the reaction product of Example XIV containing the compound having the structure:

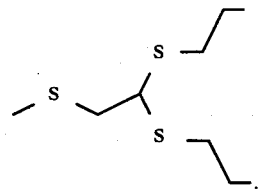

FIG. 9 is the NMR spectrum for the compound having the structure:

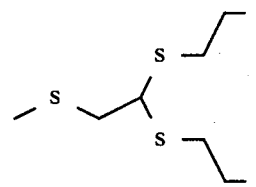

produced according to Example XIV (conditions: Field strength: 100 MHz; Solvent: CFCl₃).

Figure 10:
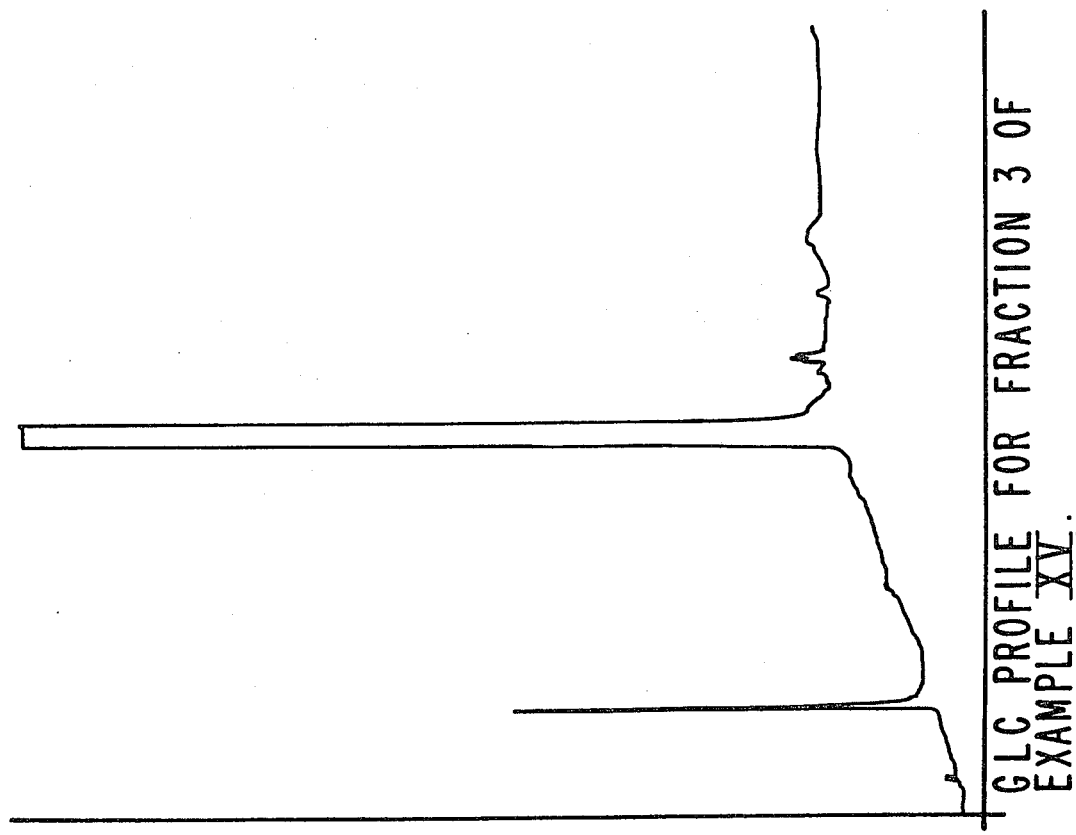

FIG. 10 is the GLC profile for Fraction 3 of the distillation product of the reaction product of Example XV containing the compound having the structure:

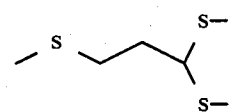

produced according to the process of Example XV (conditions: Field strength: 100 MHz; Solvent: CFCl₃).

FIG. 11 is the GLC profile for the crude reaction product of Example XVI containing the compound having the structure:

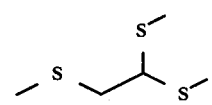

(conditions: 10'×0.125" SE-30 column programmed at 100°–220° C. at 8° C. per minute).

Figure 12:
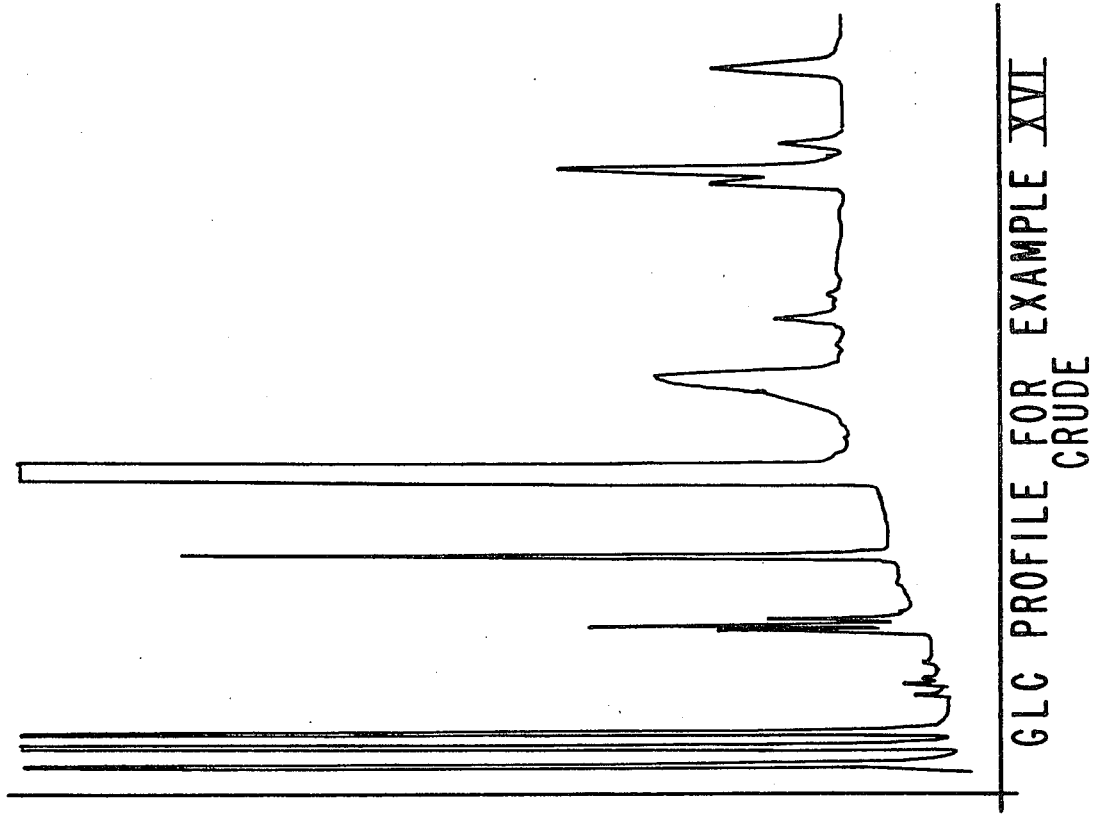

FIG. 12 is GLC profile for the crude reaction product of Example XVI containing the compound having the structure:

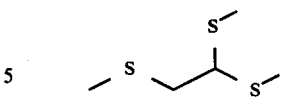

(conditions: 10'×0.125" SE-30 column, programmed at 100°–220° C. at 8° C. per minute).

Figure 13:
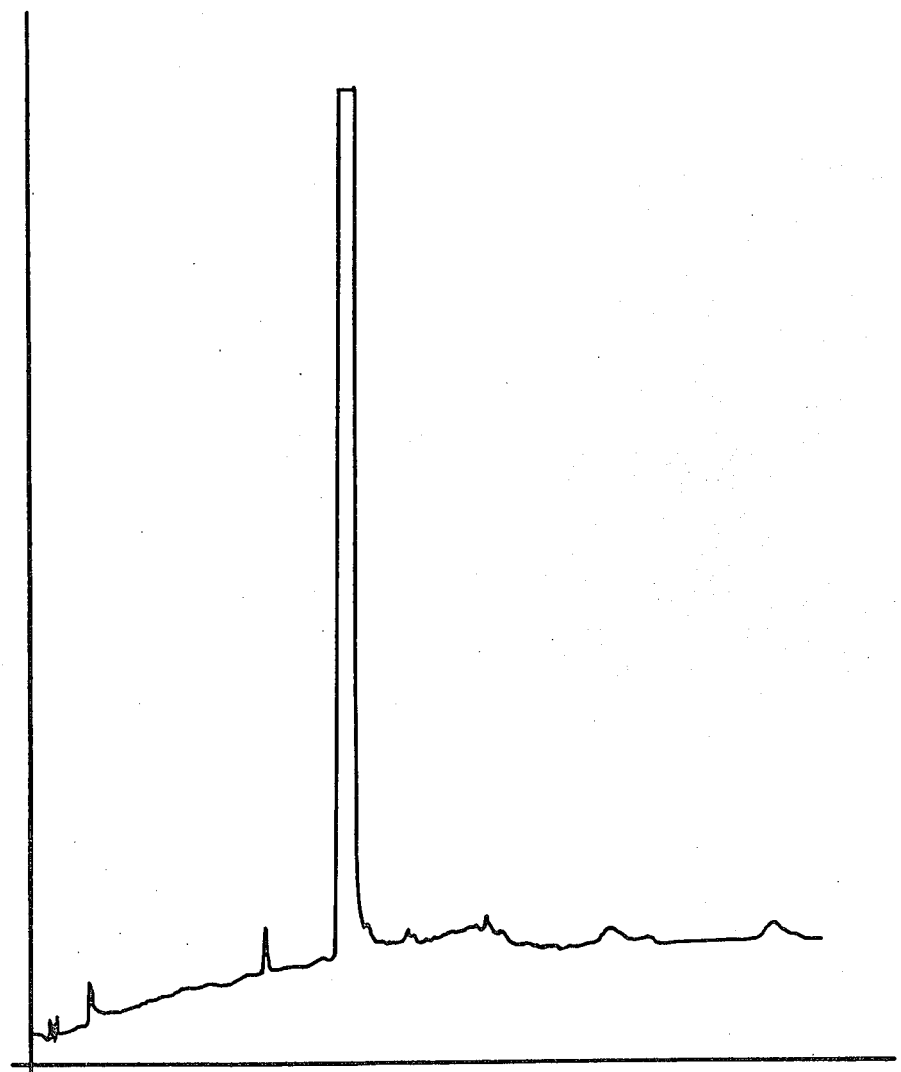

FIG. 13 is the GLC profile Fraction 3 of the distillation product of the reaction product of Example XVI containing the compound having the structure:

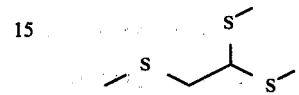

FIG. 14 is the NMR spectrum for the compound having the structure:

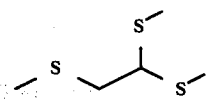

produced according to Example XVI (conditions: Field strength: 100 MHz; Solvent: CFCl₃).

DETAILED DESCRIPTION OF THE DRAWINGS

Figure 1:
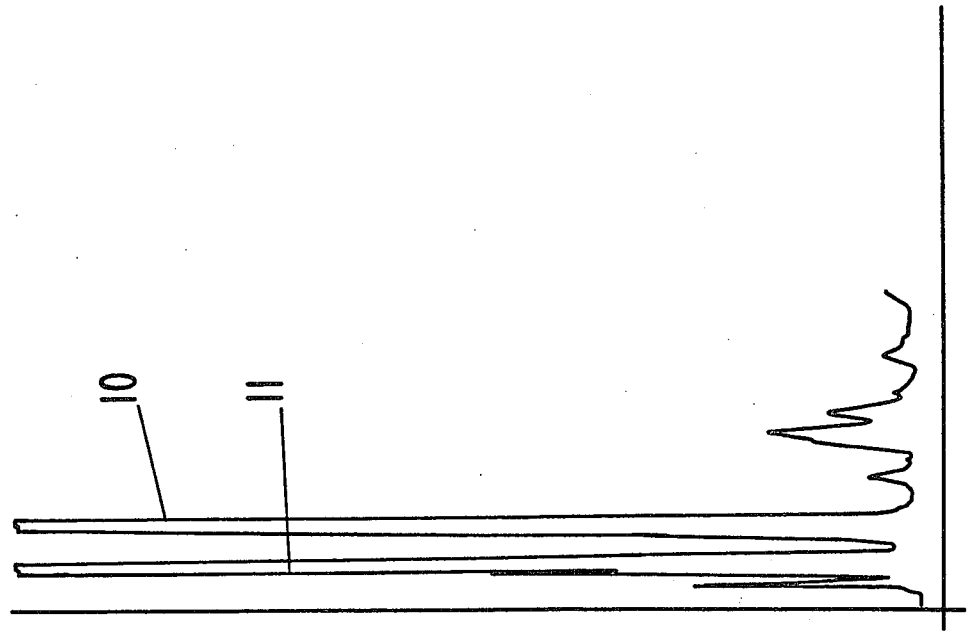
FIG. 1 is the GLC profile of the crude reaction product of Example I containing the compound having the structure.

FIG. 1 is the GLC profile for the crude reaction product of Example I containing the compound having the structure:

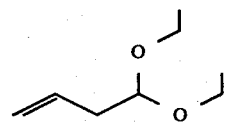

(conditions: Carbowax column programmed at 100°–220° C. at 8° C. per minute).

The peak indicated by reference numeral "10" is the peak for the compound defined according to the structure:

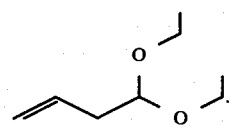

The peak indicated by reference numeral "11" is the peak for the solvent CH₂Cl₂.

FIG. 2 is the GLC profile for the crude reaction product of Example II containing the compound having the structure:

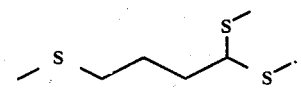

The peak indicated by reference numeral "20" is the peak for the product having the structure:

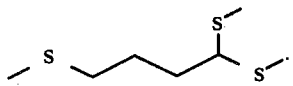

FIG. 3 is the GLC profile for Fraction 1 of the distillation product of the reaction product of Example II containing the compound having the structure:

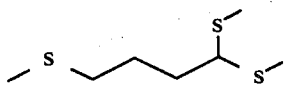

(Conditions: Carbowax column programmed at 100°–220° C. at 8° C. per minute).

The peak indicated by reference numeral "30" is the peak for the compound defined according to the structure:

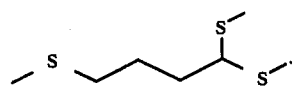

FIG. 4 is the GLC profile for Fraction 5 of the distillation product of the reaction product of Example II containing the compound having the structure:

(Conditions: Carbowax column programmed at 100°–220° C. at 8° C. per minute).

The peak indicated by reference numeral "40" is the peak for the compound having the structure:

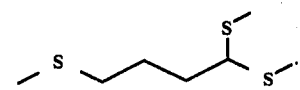

THE INVENTION

The present invention provides the novel compounds defined according to the generic structure:

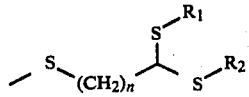

wherein n is an integer of from 1 up to 3; and wherein $R_1$ and $R_2$ are the same or different $C_1$–$C_3$ alkyl; a novel process for preparing one of such compounds defined according to the structure:

The present invention also affords methods for imparting, augmenting or enhancing various fruit, vegetable, cheese, tuna, fish and hydrolyzed vegetable protein-like flavors to consumable materials including foodstuffs, chewing gums, medicinal products and toothpastes and also provides "monosodium glutamate-like" effects in augmenting or enhancing the tastes of foodstuffs.

Briefly, the methods of the present invention contemplate the addition of compounds defined according to the genus:

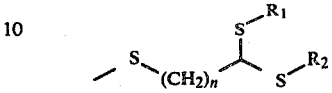

wherein n is an integer of from 1 up to 3; and wherein $R_1$ and $R_2$ are the same or different $C_1$–$C_3$ alkyl; to consumable materials, sufficient to alter the organoleptic properties of the consumable materials. The invention further contemplates a novel process for the production of one of the members of this genus defined according to the structure:

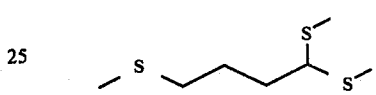

according to the reaction sequence:

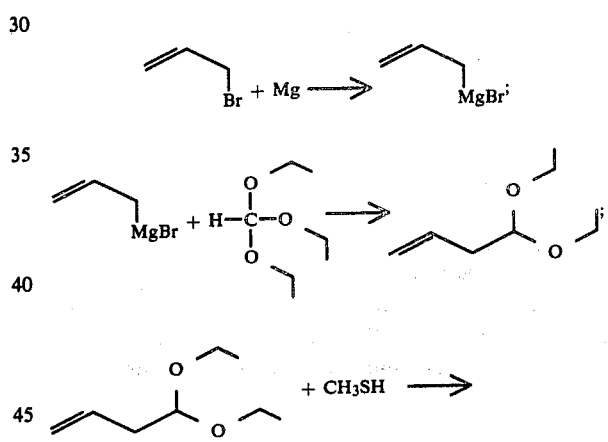

and

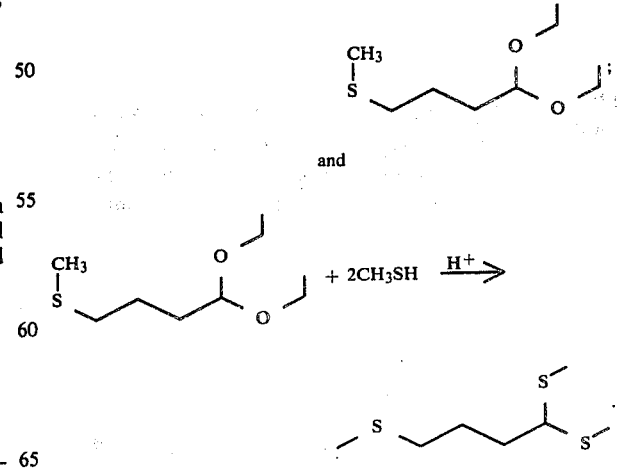

Thus, the present invention contemplates the use the compound having the structure:

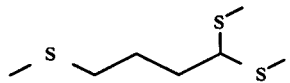

having a lichee nut-like, chinese radish-like, fruity and surface-ripened cheese aroma and taste profile particularly for augmenting or enhancing passionfruit, mango, strawberry and pineapple flavors and aromas in foodstuffs, chewing gums, toothpastes and medicinal products.

The production of the compound defined according to the structure:

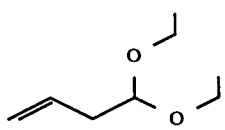

is known in the prior art and is disclosed in U.S. Pat. No. 3,904,556 issued on Sept. 9, 1975, the specification for which is incorporated by reference herein. Indeed, the preparation of the compound defined according to the structure:

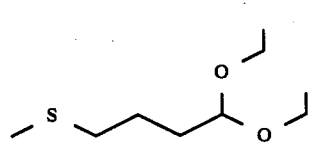

is also set forth in U.S. Pat. No. 3,904,556 issued on Sept. 9, 1975 as well as in U.S. Pat. No. 3,870,800, the specification for which is incorporated by reference herein. However, heretofore when the compound defined according to the structure:

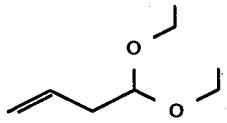

was reacted with 1 mole of methyl mercaptan, the compound having the structure:

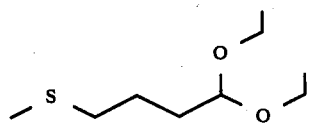

was formed according to the reaction:

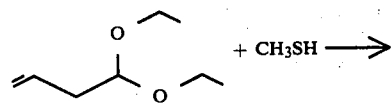

-continued

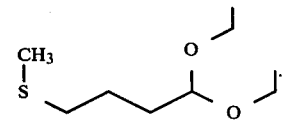

When this compound was further reacted with acid, the diethoxy moiety hydrolyzed thereby forming the compound defined according to the structure:

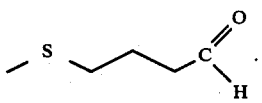

Surprisingly, however, when excess methyl mercaptan is incorporated into the reaction mass; that is, when two moles of methyl mercaptan are incorporated into the reaction mass in the presence of acid, then the reaction which takes place is as follows:

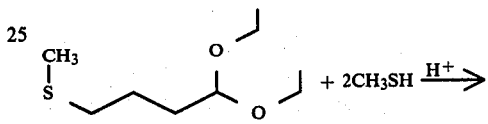

In carrying out the processes of U.S. Pat. No. 3,904,556, particularly with reference to the carrying out of Example XIII, the 1,1-diethoxy-4-(methylthio)butane having the structure:

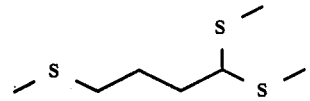

was isolated and then hydrolyzed in the presence of acid without the presence of additional methyl mercaptan. In an effort to expedite the reaction, it was attempted to carry on the reaction to form the 4-(methylthio)butanal in one reaction vessel and use a slight excess of methyl mercaptan in order to speed the reaction to completion. However, when adding the excess methyl mercaptan, the reaction:

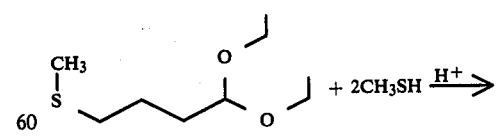

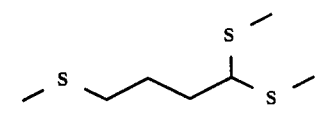

took place in a surprising and unexpected and advantageous manner.

Accordingly, the process of our invention is one which incorporates the reaction:

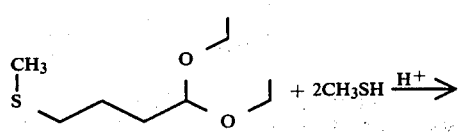

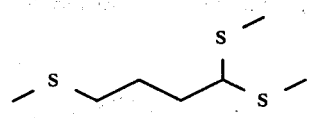

and the reactions leading up to the synthesis of the compound defined according to the structure:

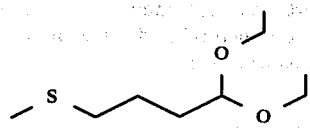

are known in the prior art; that is, known in U.S. Pat. No. 3,904,556 as well as U.S. Pat. No. 3,870,800.

In carrying out this reaction the mole ratio of methyl mercaptan to the compound defined according to the structure:

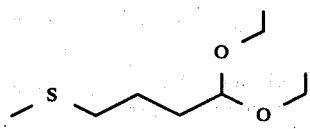

is about 2:1 and the mole ratio of methyl mercaptan used to the compound defined according to the structure:

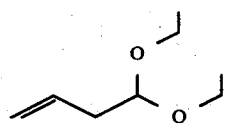

is about 3:1 or more. Since the reactions:

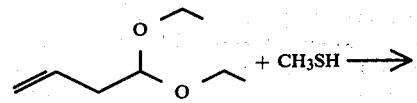

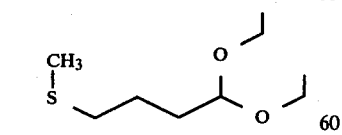

and

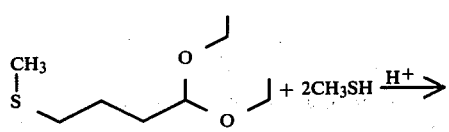

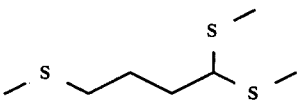

are carried out in one reaction vessel; that is, "in situ", the mole ratio of methyl mercatan to the compound defined according to the structure:

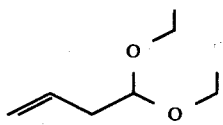

is what is most relevant.

As stated, at column 6, line 60, of U.S. Pat. No. 3,904,556 the acetal starting material having the structure:

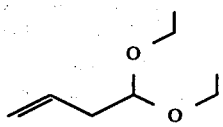

is prepared by reacting triethyl orthoformate with an allyl magnesium halide such as allyl magnesium chloride or allyl magnesium bromide. The acetal having the structure:

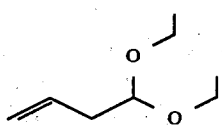

is then admixed with methyl mercaptan and exposed to ultra-violet radiation which provides the 4-(methylthio)-butyraldehydediacetal which has the structure:

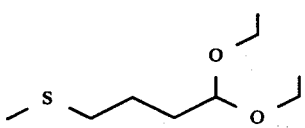

which is then reacted with additional methyl mercaptan in the presence of dilute acid in order to obtain the compound having the structure:

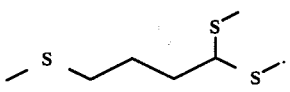

The ultra-violet irradiation is carried out at temperatures of from about −40° C. up to about +40° C. in order to give good completeness with control of the reaction velocity. The reaction can be carried out under atmospheric or super atmospheric conditions and atmospheric pressure is preferred. The ratio of mercaptan to acetal is from 3:1 up to about 6:1. The acid which is used at the subsequent part of this reaction sequence, wherein the reaction:

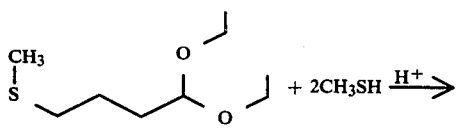
+ 2CH₃SH $\xrightarrow{H^+}$

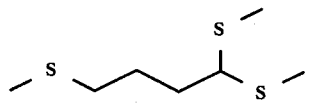

takes place may be any mineral acid which will provide the H₃O + ion such as dilute sulphuric acid, dilute phosphoric acid, dilute hydrochloric acid, dilute para-toluene sulphonic acid or the like. The acidification reaction takes place at a temperature in the range of from about 50 up to about 150° C. with temperatures of from about 120 up to about 130° C. being preferred. At the end of the reaction, the reaction mass is extracted with a solvent such as methylene dichloride and the extract is dried, filtered and stripped of solvent and then fractionally distilled. The distillation fractions may be further refined as by commercial preparative chromatography techniques in order to yield substantially pure compound defined according to the structure:

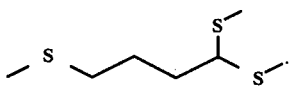

The alkylthioalkanal dialkyl mercaptals of our invention can also be produced by reacting methylthioalkanals defined according to the structure:

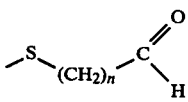

wherein n is an integer of from 1 up to 3 with an alkyl mercaptan defined according to the formula:

R,SH or defined according to the formula:

R₂SH or a mixture of alkyl mercaptans defined according to the formulae:

R,SH and

R₂SH in the presence of a protonic acid catalyst such as phosphoric acid, sulfuric acid, or para toluene sulphonic acid and in the presence of a solvent inert to the reactants and the reaction product and having a boiling point high enough so that the reaction can be carried out at reflux temperatures at atmospheric pressure, such as cyclohexane or alkyl substituted cyclohexanes. The reaction temperature is in the range of from about 50° C. up to about 110° C. when the reaction is carried out at 1 atmosphere pressure. The reaction time may vary from about 1 hour up to about 10 hours. The mole ratio of mercaptan having the structure:

R,SH or a mixture of mercaptans having the structure:

R,SH and

R₂SH to methylthioalkanal having the structure:

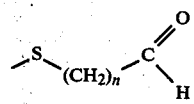

is about 2:1 or slightly greater than 2:1 since mole ratios of alkyl mercaptane:methylthioalkanal of less than 2:1 will give rise to undersired side products, hemithioacetals. At the end of the reaction, the reaction mass is purified according to standard procedures such as extraction, and fractional distillation. Overall, the reaction may be illustrated thusly:

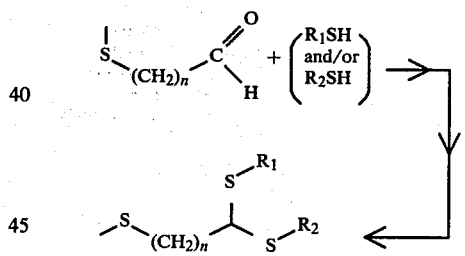

wherein n represents an integer of from 1 to 3 and R₁ and R₂ are the same or different and each represents C₁–C₃ lower alkyl, e.g., methyl, ethyl, n-propyl and i-propyl.

The following structures are illustrative of compounds prepared according to our invention and these compounds have organoleptic properties as set forth in the following table:

TABLE I

A. Methylthioalkanal Dialkyl Mercaptal

| Compound has the structure: | Flavor Property |
|---|---|
| 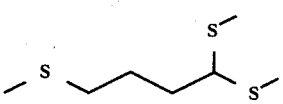 | A lichee nut-like, chinese radish-like, fruity and surface ripened cheese aroma and taste profile. |

TABLE I-continued

| A. Methylthioalkanal Dialkyl Mercaptal | Flavor Property |
|---|---|
| Compound has the structure: 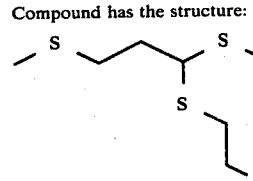 | A tomato puree, garlic and earthy aroma and taste profile at 1 ppm. A geosmine cooked potato, meat extract-like hydrolyzed vegetable protein-like and stewed meat-like aroma profile with an earthy, geosmine-like, hydrolyzed vegetable protein-like and meat extract-like taste profile at 0.1 ppm. |
| Compound has the structure: 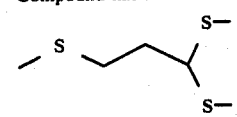 | A tuna fish, brothy, hydrolyzed vegetable protein-like, vegetable-like aroma profile with a tuna fish-like, hydrolyzed vegetable protein-like and vegetable-like taste profile at 0.1 ppm, with an effect imparted to foodstuffs closely similar to that of mono sodium glutamate. |
| Compound has the structure: 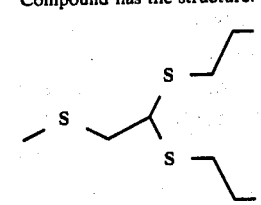 | A beef broth-like, hydrolyzed vegetable protein-like, meat extract-like, vegetable-like and fresh onion-like aroma and taste profile at 0.1 ppm having an effect closely similar to that of mono sodium glutamate in enhancing foodstuff flavors. |
| Compound has the structure: 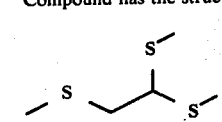 | A vegetable-like, roasted-like and hydrolyzed vegetable protein-like aroma and taste profile at 0.1 ppm with a hydrolyzed vegetable protein-like after taste. |

Our invention also concerns mixtures (primarily for use with tropical fruit flavors) of the compound having the structure:

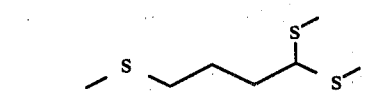

together with oxathianes defined according to the structures:

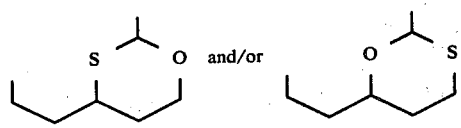

in a mole ratio of from about 1:10 down to aboue 10:1 of the compound having the structure:

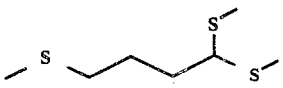

to oxathiane defined according to one of the structures:

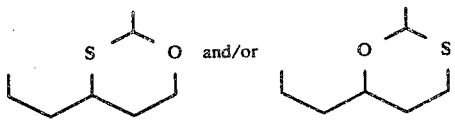

When the methylthioalkanal dialkyl mercaptals and mixtures of same with oxathianes of our invention are used as food flavor adjuvants or chewing gums, medicinal products or toothpaste adjuvants, the nature of the co-ingredients included with the methylthioalkanal dialkyl mercaptals and mixtures of same with oxathianes of our invention used in formulating the product composition will also serve to alter, modify, augment or enhance the organoleptic characteristics of the ultimate consumable material treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used hereto to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended herein to mean a composition which comprises a substantially water-insoluble, chewable plastic gum base such as chickle, or substitutes therefor, including jelutong, guttakay, rubber or certain cosmetible natural or synthetic resins or waxes. Incorporated with the gum base in admixture therewith may be plasticizers of softening agents, e.g., glycerine, and a flavoring composition which incorporates one or more of the methylthioalkanal dialkyl mercaptals and mixtures of same with oxathianes of our invention, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious, particularly from an organoleptic standpoint whereby the ultimate flavor and/or aroma of a consumable material used is not caused to have unacceptable aroma and taste nuances. Such materials may in general be characterized as flavoring agents or vehicles comprising broadly stabilizers, thickeners, surface agents, conditions, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth, gelatin, proteinaceous materials, lipids, carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, tumeric and curcuma and the like; firming agents such as aluminum sodium sulfate, calcium chloride and calcium gluconate; texturizers, anticaking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-cis-3-pentenoic acid; ketones and aldehydes, e.g., acetaldehyde, acetophenone, acetone, acetyl methyl carbinol, acrolein, n-butanal, crotonal, diacetyl, 2-methyl butanal, beta,-beta-dimethylacrolein, methyl-n-amyl ketone, n-hexanol, isopentanal, hydrocinnamic aldehyde, cis-3-hexenal, 2-heptanal, n-nonyladehyde 4-(p-hydroxy-phenyl)-2-butanone, alpha-ionone, beta-ionone, methyl-3-butanone, benzaldehyde, β-damascone, β-damascenone, acetophone, 2-heptanone, o-hydroxyacetophone, 2-methyl-2-hepten-6-one, 2-octanone, 2-undecanone, 3-phenyl-4-pentenal, 2-phenyl-2-hexanal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol,1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl capropate, ethyl caprylate, ethyl cinnamate, ethyl crontonate, ethyl formate, ethyl isobutyrate, ethyl isovalerate, ethyl laurate, ethyl myristate, ethyl alphamethylbutyrate, ethyl propionate, ethyl salicylate, trans-2-hexenyl acetate, hexyl acetate, 2-hexenyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, n-dodecane, methyl diphenyl, methyl naphthalene, mycrene, naphthalene, n-octadecane, n-tetradecane, tetramethyl naphthalene, n-tridecane, trimethyl naphthalene, undecane, caryophyllene, 1-phellandrene, p-cymene and 1-alpha-pimene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, 2-isopropyl-4,5-dimethylpyrazine, 2-methyl-3-ethylpyrazine, tetramethylpyrazine, trimethylpyrazine, essential oils, such as jasmine absolute, cassia oil, cinnamon bark oil, rose absolute, orris absolute, lemon essential oil, Bulgarian rose, yara yara and vanilla, lactones such as delta nonalactone, gamma nonalactone, delta dodecalactone, gamma dodecalactone, sulfides, e.g, methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the methylthioalkanal dialkyl mercaptals and mixtures of same with oxathianes of our invention by not covering or spoiling the organoleptic properties (aroma and/or taste) thereof; (ii) be non-reactive with the methylthioalkanal dialkyl mercaptals and mixtures of same with oxathianes of our invention and (iii) be capable of providing an environment in which the methylthioalkanal dialkyl mercaptals and mixtures of same with oxathianes of our invention can be dispersed or admixed to provide a homogeneous medium. In addition, selection of one or more flavoring adjuvants, as well as the quantities thereof will depend upon the precise organoleptic character desired in the finished product. This, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the methylthioalkanal dialkyl mercaptals and mixtures of same with oxathianes of our invention employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavor composition.

The use of insufficient quantities of methylthioalkanal dialkyl mercaptals and mixtures of same with oxathianes of our invention will, of course, substantially vitate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of methylthioalkanal dialkyl mercaptals and mixtures of same with oxathianes ranging from a small but effective amount, e.g., 0.0003 parts per million up to about 300 parts per million based on total composition are suitable. Concentrations in excess of the maximum quantity stated are not normally recommended, since they fail to provide commensurate enhancement of organoleptic properties. In those instances, wherein methylthioalkanal dialkyl mercaptals and mixtures of same with oxathianes of our invention are added to the foodstuff as an integral component of a flavoring composition, it is, of course, essential that the total quantity of flavoring composition employed be sufficient to yield an effective concentration of methylthioalkanal dialkyl mercaptals and mixtures of same with oxathianes of our invention in the foodstuff product.

Food flavoring compositions prepared in accordance with the present invention preferably contain methylthioalkanal dialkyl mercaptals and mixtures of same with oxathianes in concentrations ranging from about 0.01% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing methylthioalkanal dialkyl mercaptals and mixtures of same with oxathianes with, for example, gum arabic, gum tragacanth, carrageenan and the like, and thereafter spray-drying the resultant mixture whereby to obtain the particularate solid product. Pre-prepared flavor mixes in powder form, e.g., fruit flavored powder mixes are obtained by mixing the dried solid compositions, e.g., starch, sugar and the like and one or more methylthioalkanal dialkyl mercaptals and mixtures of same with oxathianes in a dry blender until the requisite degree of uniformity is achieved.

It is presently preferred to combine with methylthioalkanal dialkyl mercaptals and mixtures of same with oxathianes of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Guaiacol;
Ethyl pelargonate;
Cinnamaldehyde;
Methyl Anthranilate;
5-Methyl furfural;
Isoamyl acetate
Isobutyl acetate;
Cuminaldehyde;
Alpha ionone;
Cinnamyl formate;
Ethyl butyrate;
Methyl cinnamate;
Acetic acid;
Gama-undecalactone;
Naphthyl ethyl ether;
Diacetyl;
Furfuryl
Ethyl acetate;
Anethole;
2,3-Dimethyl pyrazine;
2-Ethyl-3-methyl pyrazine;
3-Phenyl-4-pentenal;
2-Phenyl-2-hexanal;
2-Phenyl-2-pentenal;
3-Phenyl-4-pentenal diethyl acetal;
$\gamma$-Terpinene;
$\delta$-Carene;
Isopropyl-bicycloheptane;
Trans-Caryophyllene;
Humulene;
Nerol;
n-Tetradecanal;
n-Hexadecanal;
2-Methylheptadecane;
9-n-Octylheptadecane;
2,6,10,14-Tetramethylhexadecane
2,6,11,15-Tetramethylhexadecane;
9-Heptadecanone;
2,6,10,15-Tetramethylheptadecane;
Beta-Damascone (1-crotonyl-2,6,6-trimethylcyclohex-1-ene);
Beta-Damascenone (1-crotonyl-2,6,6-trimethylcyclohexa-1,3-diene);
Beta-cyclohomocitral (2,6,6-trimethylcyclohex-1-ene carboxaldehyde);
Isoamyl butyrate;
Cis-3-hexanol-1;
2-Methyl-2-pentenoic acid;
Elemecine (4-allyl-1,2,6-trimethoxybenzene);
Isoelemecine (4-propenyl-1,2,6-trimethoxybenzene);
2-(4-Hydroxy-4-methylpentyl)norbornadiene;
2-(4-Hydroxy-4-methylpentyl) norbornadiene;

Mono sodium glutamate;
2-Methyl-3-furanthio
4-(Methylthio) butanal;
Ethyl-4-(methylthio) butyrate;
4-(Methylthio) butanal;
2,5-Dimethyl Furan-3-thiol;
2,5-Dimethyl-3-Furan thioacetate;
2-Methyl-3-Furan thioisobutyrate;
Reaction product of hydrogen sulfide and Maltol; and
Reaction product of hydrogen sulfide and ethyl maltol.

The following Examples I and II set forth a process for preparing the 4-(methylthio)-butyraldehyde-dimethyl mercaptal. Examples III–XII set forth organoleptic uses of 4-(methylthio)butyraldehyde-dimethyl mercaptal of our invention. Examples XII–XVI set forth processes for preparing other methylthioalkanal dialkyl mercaptals of our invention. Examples XVII et seq., set forth organoleptic uses of methylthioalkanal dialkyl mercaptals of our invention. All parts and percentages are by weight unless otherwise specified. These examples are not by way of limitation but are only by way of illustration. This patent is intended only to be limited by the scope of the claims, infra.

EXAMPLE I

Preparation of 1,1-Diethoxy-3-Butene

Reaction:

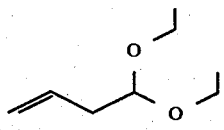

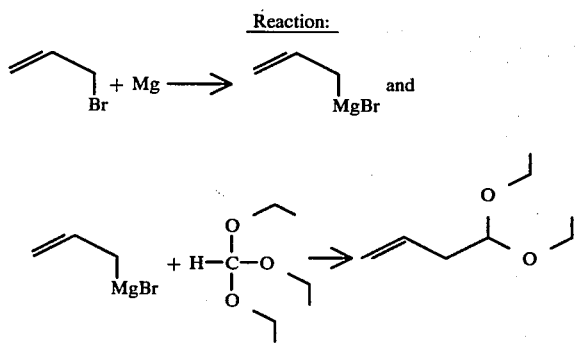

A 12-liter reaction flask equipped with a reflux condenser, mechanical stirrer, dropping funnel, a drying tube and isopropanol cooling bath is charged with 264 grams of magnesium turnings and 3-liters of diethyl ether.

The reaction mass is stirred whereupon 60 grams of allyl bromide is added thereto over a period of two hours while maintaining reflux. Reflux is continued for a period of four hours. The reaction mass is then cooled to 5°–10° C. Over a period of two hours while maintaining the reaction mass at 5°–10° C., 1,530 grams of triethyl orthoformate is added to the reaction mass over a period of three hours.

The reaction mass is then refluxed for a period of four hours.

Sufficient hydrochloric acid is then added to the reaction mass to bring the pH down to 4.5. The reaction mass is then neutralized with a 5% sodium bicarbonate solution to bring the pH back up to 6.8. The reaction mass is then extracted with three 1-liter portions of methylene dichloride. The organic phases are combined. The solvent is then stripped and the reaction mass is distilled on a 4″ splash column, packed with saddles yielding the following fractions:

| Fraction No. | Vapor Temp. (°C.) | Liquid Temp. (°C.) | Vacuum mm/Hg. Pressure |
|---|---|---|---|
| 1 | 37/ | 50/ | 8 |
| 2 | 37 | 51 | 6 |
| 3 | 37 | 54 | 6 |
| 4 | 38 | 62 | 6 |
| 5 | 40 | 92 | 2 |
| 6 | 70 | 146 | 1 |
| 7 | 75 | 200 | 1 |

The resulting product has the structure:

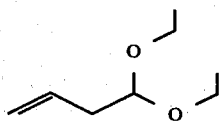

FIG. 1 is the GLC profile for the crude reaction product. The peak indicated by reference numeral "10" is the peak for the product having the structure:

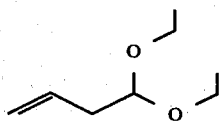

(conditions: Carbowax column, programmed at 100°–220° C. at 8° C. per minute).

The peak indicated by reference numeral "11" is the peak for the solvent $CH_2Cl_2$.

EXAMPLE II

Preparation of
4-(Methylthio)-(Butyraldehyde-Dimethyl Mercaptal

Reaction:

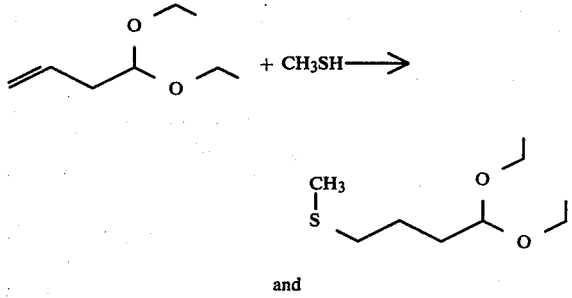

and

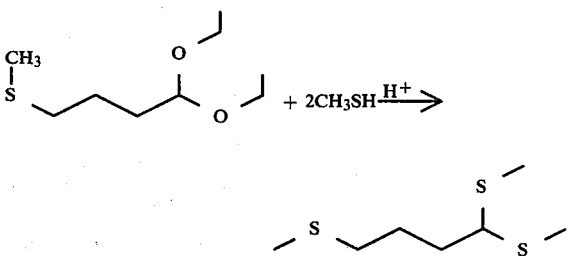

A 2-liter, three-neck flask equipped with a magnetic stirrer, dry ice condenser, and thermometer and a 450 watt high pressure Hanovia UV lamp is charged with 100 grams of 1,1-diethoxy-3-butene (prepared according to the process of Example I).

The contents of the flask are cooled to 0° C. and 50 grams of methanethiol is added. Using a dry ice-isopropanol cooling bath as well as a condenser, the temperature of the reaction mass is maintained at 0° C. while UV light is directed at the flask for a period of 15 minutes. The temperature of the reaction mass is allowed to rise to +30° C. at which point the UV light is shut off. The reaction mixture is then cooled to 15° C. and the UV light is again turned on and the reaction mass is exposed to UV light for an additional 25 minutes, at which point the reaction temperature rises to 42° C. The UV light has been shut off and the reaction mass is cooled to 15° C. whereupon the UV light is turned on for 25 minutes and the temperature of the reaction mass is allowed to increase to 45° C. The UV light is then shut off, the reaction mass is cooled to 0° C. and an additional 50 grams of methanethiol is added. The UV light is then turned on for another 45 minutes and the reaction mass temperature rises to 15° C. The reaction mass is cooled to room temperature and a mixture of 250 ml water and 50 ml concentrated sulphuric acid is added thereto with stirring. The reaction mass is maintained at 22°–26° C. for a period of four hours. At the end of this time, the reaction mass is transferred to 2-liter separatory funnel and extracted with five 200 ml portions of methylenedichloride. The extracts are combined and washed with one 200 ml portions of saturated sodium chloride solution. The extracts are then dried over anhydrous sodium sulphate, filtered and distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 95/ | 106/ | 4 |
| 2 | 110 | 114 | 3 |
| 3 | 111 | 113 | 3 |
| 4 | 112 | 118 | 2 |
| 5 | 180 | 220 | 2 |

From an organoleptic standpoint the resulting product has a lichee nut-like, chinese radish-like, surface-ripened cheese-like and fruity aroma and taste profile at a level of 0.001 ppm.

FIG. 2 is the GLC profile of the reaction product prior to distillation. The peak indicated by reference numeral "20" is the peak for the compound having the structure:

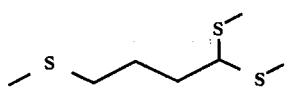

(Conditions: Carbowax column, programmed at 100°–220° C. at 8° C. per minute).

FIG. 3 is the GLC profile for Fraction of the foregoing distillation. The peak indicated by reference numeral "30" is the peak for the compound having the structure:

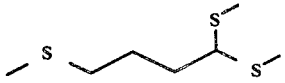

(Conditions: Carbowax column, programmed at 100°–220° C. at 8° C. per minute).

FIG. 4 is the GLC profile for Fraction 5 for Fraction 5 of the foregoing distillation. The peak indicated by reference numeral "40" is the peak for the compound having the structure:

(Conditions: Carbowax column, programmed at 100°–220° C. at 8° C. per minute).

FIG. 5 is the NMR spectrum for Fraction 5 of the foregoing distillation. The compound in Fraction 5 having the structure:

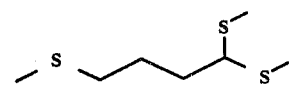

(Conditions: $CFCl_3$ solvent; 100 MHz field strength).

EXAMPLE III

Beverage

Goya Products Inc. Mango Nectar is flavored at a level of 0.001 ppm with the compound having the structure:

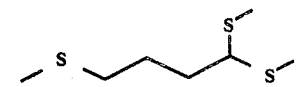

produced according to Example II (Fraction 5). The resulting mango nectar has a much more natural-like, freshly picked mango nuance unlike standard mango nectar. When the compound having the structure:

is replaced with a 2:8 (mole:mole) mixture of oxathiane having the structure:

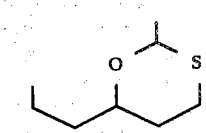

in admixture with the compound having the structure:

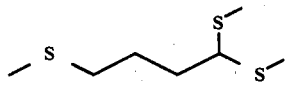

a more intense fresh note with the same natural mango aroma and taste nuances are present.

EXAMPLE IV

Mango Flavor

The following flavor formulation is prepared:

| Ingredients | Parts by Weight |
|---|---|
| The compound having the structure: 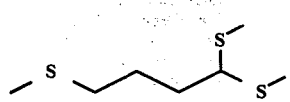 | 8.0 |
| γ-Terpinene | 14.0 |
| δ-Carene | 32.0 |
| Isopropyl-bicycloheptane | 18.0 |
| Trans-Caryophyllene | 28.0 |
| Humulene | 22.4 |
| Nerol | 18.0 |
| Tetradecanol | 4.0 |
| Hexadecanol | 14.0 |
| 2-Methylheptadecane | 82.0 |
| 9-n-Octylheptadecane | 50.0 |
| 2,6,10,14-Tetramethylhexadecane | 24.0 |
| 2,6,11,15-Tetramethylhexadecane | 21.0 |
| 9-Heptadecanone | 14.0 |
| 2,6,10,15-Tetramethylheptadecane | 4.0 |
| Trans,trans,delta damascone | 2.0 |

The compound defined according to the structure:

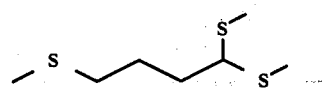

imparts a fresh, natural lichee nut, lactonic natural nuance with pineapple-like and passionfruit-like nuances to this mango flavor. The resulting mango flavor without the compound having the structure:

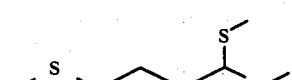

has a very bland standard "canned fruit" taste and aroma and does not have the natural intense fresh character that the formulation has with the use of the compound having the structure:

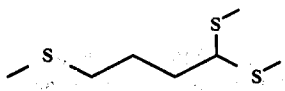

EXAMPLE V

The following mixture is prepared:

| Ingredients | Parts by Weight |
|---|---|
| Natural Strawberry Concentrate | 2.5% |
| Strawberry Juice | 85.0% |
| Water | |
| Sugar syrup (37.5° Baume) | 15.5% |

The fresh strawberry note of the strawberry juice is imparted in increased strength by addition of the compound defined according to the structure:

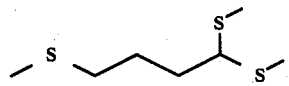

prepared according to Example I, at a rate of from 0.002 up to 2 ppm. The aroma and taste is further enhanced by the addition of from 0.2 up to 1 ppm of 2-methyl-2-pentenoic acid.

EXAMPLE VI

To the mango flavor composition as set forth in Example IV is added at a rate of 0.2% to various foodstuffs with and without the compound having the structure:

When it is added with the compound having the structure:

it is called the "test composition. When it is added without the chemical having the structure:

it is called the "control composition".

The test and control compositions are added to the food products described hereinafter in the proportions shown for 10 kilograms of material to be flavored:
Pudding: 5–10 grams (0.15–0.1%),
Cooked sugar: 15–20 grams (0.15–2%).
[Cooked sugar preparation: 100 ml of sugar syrup (prepared by dissolving 1 kilogram of sucrose in 600 ml of water) and 20 grams of glucose are mixed together and slowly heated to 145° C. The flavor is added and the mass is allowed to cool and harden.]
[Pudding preparation: To 500 ml of warmed milk are added with stirring a mixture of 60 grams sucrose and 3 grams of pectin. The mixture is boiled for a few seconds and the flavor is added. The mixture is allowed to cool.]
The finished foodstuff samples are tested by a panel of trained persons who express their views about the flavor of the samples. All members of the panel prefer the test samples having a more distinguished fresh strawberry aroma with faint tropical nuances and lichee nut notes.

EXAMPLE VII

A. Powder Flavor Composition

20 Grams of the flavor composition of Example III containing the compound having the structure:

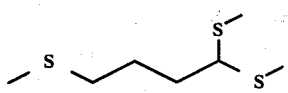

prepared according to Example I, is emulsified in a solution containing 300 grams of gum acacia and 700 grams water. The emulsion is spray-dried with a Bowen Lab Model Drier utilizing 260 c.f.m. of air with an inlet temperature of 500° F., an outlet temperature of 250° F., and a wheel speed of 50,000 rpm.

B. Sustained Release Flavor

The following mixture is prepared:

| Ingredients | Parts by Weight |
|---|---|
| Liquid Mango Flavor of Example III | 20.00 |
| Propylene Glycol | 9.00 |
| Cab-O—Sil ® M-5: (Brand of silica produced by the Cabot Corporation of 125 High Street, Boston, Mass. 02112; Physical Properties: Surface area: 200 M$^2$/gm Nominal particle size: 0.012 microns Density: 2.3 lbs/cu. ft.) | 5.00 |

The Cab-O-Sil is dispersed in the liquid mango flavor composition of Example III, with vigorous stirring, thereby resulting in a viscous liquid. 71 Parts by weight of the powder flavor composition of Part A, supra, is then blended into the said viscous liquid, with stirring at 25° C. for a period of thirty minutes resulting in a dry, free flowing sustained release mango flavor powder.

EXAMPLE VIII

10 Parts by weight of a 5- Bloom pigskin gelatin is added to 90 parts by weight of water at a temperature of 150° F. The mixture is agitated until the gelatin is completely dissolved and the solution is cooled to 120° F. 20 Parts by weight of the liquid mango flavor composition of Example III is added to the solution which is then homogenized to form an emulsion having a particle size typically in the range of 5-40 microns. This material is kept at 120° F. under which conditions the gelatin will not gel.

Coacervation is induced by adding, slowly and uniformly, 40 parts by weight of a B 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting gelled coacervate may be filtered and washed with water at temperatures below the melting point of gelatin, to remove the salt.

EXAMPLE IX

Chewing Gum

100 Parts by weight of chicle are mixed with 4 parts by weight of the flavor prepared in accordance with Example VI-B. 300 Parts of sucrose and 100 parts of corn syrup are added. Mixing is effected in a ribbon blender with jacketed side walls of the type manufactured by the Baker Perkins Co.

The resultant chewing gum blended is then manufactured into strips 1 inch in width and 0.1 inches in thickness. The strips are cut into lengths of 3 inches each. On chewing, the chewing gum has a pleasant, long lasting mango flavor.

EXAMPLE X

Chewing Gum

100 Parts by weight of chicle are mixed with 18 parts by weight of the flavor prepared in accordance with Example VII. 300 Parts of sucrose and 100 parts of corn syrup are added. Mixing is effected in a ribbon blender with jacketed walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting mango flavor.

EXAMPLE XI

Toothpaste Formulation

The following separate groups of ingredients are prepared:

| Parts by Weight | Ingredients |
|---|---|
| GROUP "A" | |
| 30.200 | Glycerine |
| 15.325 | Distilled Water |
| .100 | Sodium Benzoate |
| .125 | Saccharin Sodium |
| .400 | Stannous Fluoride |
| GROUP "B" | |
| 12.500 | Calcium Carbonate |
| 37.200 | Dicalcium Phospate (Dihydrate) |
| GROUP "C" | |
| 2.000 | Sodium n-Lauroyl Sarcosinate (foaming agent) |
| GROUP "D" | |
| 1.200 | Flavor Material of Example VI-B |
| 100.00 (Total) | |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste, when used in a normal toothbrushing procedure yields a pleasant mango flavor, of constant strong intensity throughout said procedure (1-1.5 minutes).

EXAMPLE XII

Chewable Vitamin Tablets

The flavor material produced according to the process of Example VI-B is added to a Chewable Vitamin Tablet Formulation at the rate of 10 grams/kilogram which chewable vitamin tablet formulation is prepared as follows:

In as Hobart Mixer the following materials are blended to homogeneity:

| | Gms/<br>1000 tablets |
|---|---|
| Vitamin C (ascorbic acid) as ascorbic acid-sodium ascorbate mixture 1:1 | 70.00 |
| Vitamin B$_1$ (thiamine mononitrate) as Rocoat ® thiamine mononitrate 33⅓% (Hoffman LaRoche) | 4.0 |
| Vitamin B$_2$ (riboflavin) as Rocoat ® riboflavin 33⅓% | 5.0 |
| Vitamin B (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate as dry vitamin E acetate 33⅓% | 6.6 |
| Roche d-biotin | |
| Flavor of Example VI-B | 0.004 (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g. Dry Vitamin A Acetate and 0.6 g Vitamin D are then added as beadlets. The entire blend is then compressed using concave punches at 0.5 g each.

Chewing of the resultant tablets yields a pleasant, long-lasting, consistenly strong mango flavor for a period of 12 minutes.

EXAMPLE XIII

Preparation of Dipropyl Mercaptal of 3-(Methylthio) Propionaldehyde

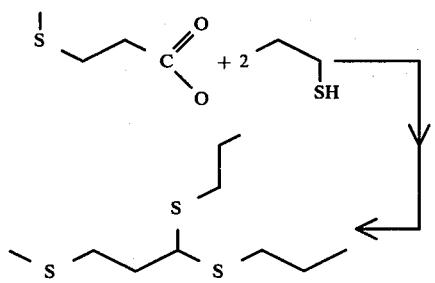

Into a 100 ml reaction flask equipped with reflux condensor, heating mantle, hot plate (with magnetic stirring apparatus build in) and stirring bar is placed 10 ml cyclohexane, 0.5 grams of para toluene sulphonic acid and 16.0 grams (0.2 moles) of n-propyl mercaptan. Over a period one hour, 10.4 grams of methional (0.1 moles) is added to the reaction mass. The reaction mass is then heated to reflux and refluxed for a period of three hours. The reaction mass is then cooled and transferred to a separatory funnel. The reaction mass is washed with 150 ml portion of saturated sodium chloride solution and dried over anhydrous sodium sulfate, filtered and distilled on a micro vigreux column yielding the following fractions:

| Fraction No. | Vapor Temp. (°C.) | Liquid Temp. (°C.) | Vacuum mm/Hg. Pressure |
|---|---|---|---|
| 1 | 129/ | 143/ | 1:0 |
| 2 | 131 | 152 | 1:0 |
| 3 | 133 | 152 | 1:0 |
| 4 | 128 | 145 | 1:0 |
| 5 | 120 | 160 | 1:0 |

FIG. 6 is the GLC profile for Fraction 3 of the foregoing distillation.

FIG. 7 is the NMR spectrum for the compound having the structure:

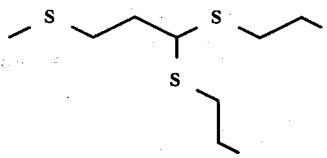

(conditions: Field strength: 100 MHz; Solvent: CFCl$_3$).

EXAMPLE XIV

Preparation of Dipropyl Mercaptal of (Methylthio) Acetaldehyde

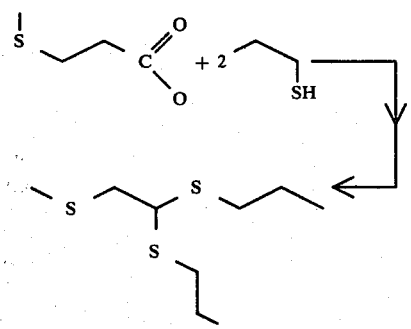

Into a 100 ml reaction flask equipped with reflux condensor, heating mantle, hot plate (with built-in magnetic stirring apparatus) and stirring bar is placed 10 ml cyclohexane, 0.5 grams para toluene sulfonic acid and 16 grams (0.2 moles) of propyl mercaptan. Over a period of one hour, 9 grams (0.1 moles) of methylthio acetaldehyde is added to the reaction mass.

The reaction mass is then heated to reflux and maintained at reflux for a period of four hours. The reaction mass is then transferred to a separatory funnel and is washed with 150 ml portion of saturated sodium chloride solution, dried over anhydrous sodium sulfate, filtered and distilled on a micro vigreux column using the following fractions:

| Fraction No. | Vapor Temp. (°C.) | Liquid Temp. (°C.) | Vacuum mm/Hg. Pressure |
|---|---|---|---|
| 1 | 90/ | 116/ | 1:0 |
| 1 | 90/ | 116/ | 1:0 |
| 2 | 101 | 130 | 1:0 |
| 3 | 110 | 138 | 1:0 |
| 4 | 120 | 143 | 1:0 |
| 5 | 90 | 160 | 1:0 |

FIG. 8 is the GLC profile for Fraction 3 of the foregoing distillation.

FIG. 9 is the NMR spectrum for the compound having the structure:

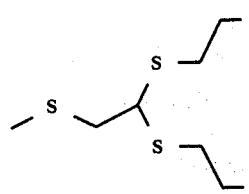

(conditions: Field strength: 100 MHz; Solvent: CFCl₃).

EXAMPLE XV

Preparation of Dimethyl Mercaptal of 3-(Methylthio) Propionaldehyde

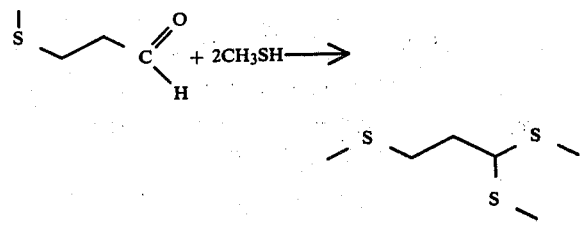

Into a 100 ml reaction flask equipped with reflux condensor, heating mantle, and hot plate (equipped with magnetic stirring apparatus) and stirring bar is placed 10 ml cyclohexane, 0.5 grams of para toluene sulphonic acid and 10 grams (0.2 moles) of methyl mercaptan. Over a period of one hour, 10.4 grams (0.1 mole) of methional is added to the reaction mass. The reaction mass is then refluxed for a period seven hours. The resulting reaction product is washed with one 50 ml portion of saturated aqueous sodium chloride and dried over anhydrous sodium sulfate, filtered and distilled on a fractional distillation column yielding the following fractions:

| Fraction No. | Vapor Temp. (°C.) | Liquid Temp. (°C.) | Vacuum mm/Hg. Pressure |
|---|---|---|---|
| 1 | 106/ | 121/ | 1:0 |
| 2 | 117 | 125 | 1:0 |
| 3 | 114 | 124 | 1:0 |
| 4 | 105 | 130 | 1:0 |

FIG. 10 is the GLC profile for Fraction 3 of the foregoing distillation.

FIG. 11 is the NMR spectrum for the compound having the structure:

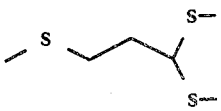

(Conditions: Field strength: 100 MHz; Solvent: CFCl₃).

EXAMPLE XVI

Preparation of Dimethyl Mercaptal of (Methylthio) Acetaldehyde

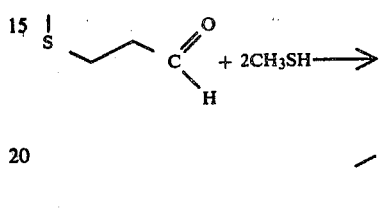

Into a 100 ml reaction flask equipped with reflux condensor, heating mantle, and hot plate (equipped with magnetic stirring apparatus) and stirring bar is placed 10 ml cyclohexane, 0.5 grams of para toluene sulphonic acid and 10 grams (0.2 moles) of methyl mercaptan. Over a period of one hour, 9 grams (0.1 mole) of methylthio acetaldehyde is added to the reaction mass. The reaction mass is then heated to reflux and maintained at reflux for a period of 8.5 hours. The reaction mass is then transferred to a separatory funnel and washed with one 50 ml portion of aqueous saturated sodium chloride, then dried over anhydrous sodium sulfate, filtered and distilled on a micro vigreux column yielding the following fractions:

| Fraction No. | Vapor Temp. (°C.) | Liquid Temp. (°C.) | Vacuum mm/Hg. Pressure |
|---|---|---|---|
| 1 | 69/ | 83/ | 1:0 |
| 2 | 90 | 97 | 1:0 |
| 3 | 90 | 105 | 1:0 |
| 4 | 75 | 120 | 1:0 |

FIG. 12 is the GLC profile of the crude reaction product (conditions: SE-30 column (10'×0.125") programmed at 100°-220° C. at 8° C. per minute.

FIG. 13 is the GLC profile for Fraction 3 of the foregoing distillation product.

FIG. 14 is the NMR spectrum for the compound having the structure:

(conditions: Field strength: 100 MHz; Solvent: CFCl₃).

EXAMPLE XVI

To a portion of a standard salad dressing, the compound prepared according to Example XIII having the structure:

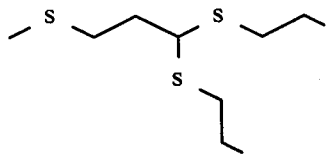

is added at the rate of 1 ppm. The resulting mixture has a characteristic tomato puree-like, garlic-like and earthy note in addition to the "salad dressing-like" profile. The salad dressing is a mixture of the following:

| Ingredient | Parts |
|---|---|
| Black pepper oil | 3 |
| Nutmeg oil | 3 |
| Celery oil | 3 |
| Lemon oil | 3 |
| Mustard oil | 1 |
| Vinegar-citric acid (50:50 mixture) | 120 |
| Starch paste prepared from tapioca flour-water (50:50 mixture) | 300 |
| Liquid egg yolks | 210 |
| Sodium chloride | 7 |
| Sucrose | 10 |
| Mustard | 20 |
| Locust Bean gum | 6 |

EXAMPLE XVIII

Potato Flavor

A potato flavoring material is prepared by admixing the following ingredients:

| Ingredients | Parts by Weight |
|---|---|
| Diacetyl (1% solution in foodgrade propylene glycol) | 0.20 |
| 2-acetyl-3-ethyl pyrazine (1% solution in foodgrade propylene glycol) | 1.0 |
| 2-ethyl-3-methyl-pyrazine | 4.0 |
| methional | 2.0 |
| 5-methyl-alpha-[(methylthio)methyl]-2-furan acrolein | 0.2 |
| Compound prepared according to Example XIII having the structure: 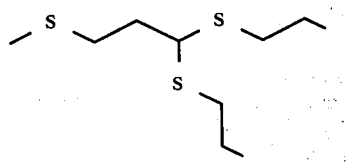 | 1.0 |
| ethanol (95% food grade) | 90.6 |

A bench panel of five individuals (not employed by the Assignee of the instant application and not knowing the nature of the test material) compared the above formulation with one not containing any compound having the structure:

but identical in all other respects. The formulations were compared at the rate of 1.0 ppm in water solutions. It was concluded that the compound having the structure:

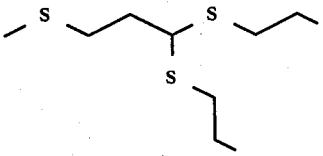

imparts to the flavor earthy, geosmine-like, cooked potato, meat extract-like, hydrolyzed vegetable protein-like and stewed metal-like aroma nuances with earthy, geosmine-like, hydrolyzed vegetable protein-like and meat extract-like taste nuances.

When the compound having the structure:

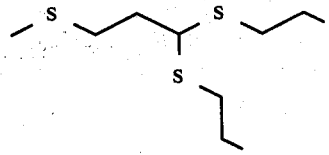

is added alone at the level of 0.1 ppm to a standard "chicken sausage" (ingredients: chicken: 50%; pork: 25%; bread filling: 25%) the flavor intensity is increased by approximately 25% as would result from the use of monosodium glutamate. Accordingly, the compound having the structure:

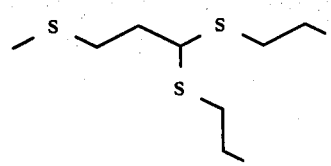

is considered to be a monosodium glutamate replacer.

EXAMPLE XIX

The compound having the structure:

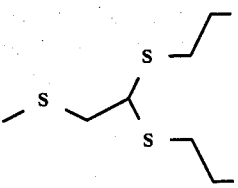

produced according to Example XIV is dissolved in propylene glycol to provide a 0.1% solution. This solution is added to 7.3 grams of a soup base (in order to yield a level of 0.01 ppm of the compound having the structure:

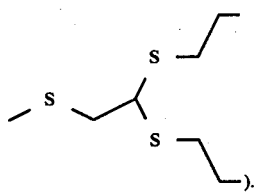

The soup base consists of:

| Ingredient | Parts by Weight |
| --- | --- |
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting beef broth flavor has a meat extract-like, fresh onion-like, vegetable-like and hydrolyzed vegetable protein-like aroma and taste profile. The compound having the structure:

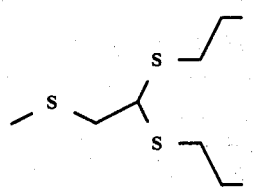

causes the flavor to be intensified by approximately 25% and brings out the natural beef-like notes of this broth. The Compound having the structure:

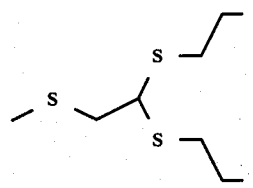

is considered by a bench panel of four independent individuals (not associated with the Assignee of the instant application) to be superior in all respects to the beef broth not containing the compound having the structure:

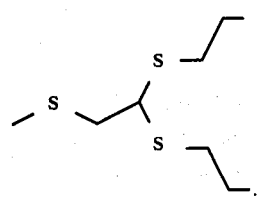

The compound having the structure:

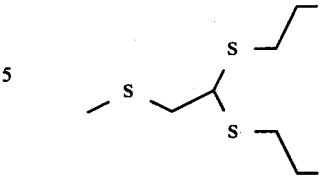

is considered to be a monosodium glutamate replacer.

EXAMPLE XX

The compound having the structure:

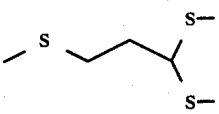

prepared according to Example XV is added to a 2% solution of commercial clam chowder:
Ingredients: Salt, water, whole clam meat, commercial fish chowder and whole crab meat
as the rate of 0.1 ppm. The resulting food has a tuna-like, natural clam chowder-like, vegetable aroma and taste profile and the compound having the structure:

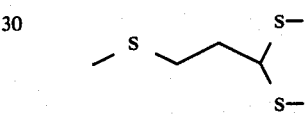

gives the resulting chowder a much greater intensity than without its use. The compound having the structure:

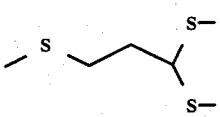

is considered to have the same affect as monosodium glutamate in flavor enhancement and intensification. In addition, the compound having the structure:

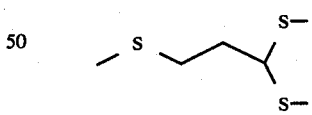

imparts a fresh tuna fish flavor to the foregoing broth.

EXAMPLE XXI

The compound having the structure:

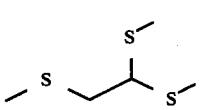

prepared according to Example XVI is added to a 2% solution of Wyler's "Beef Flavored Instant Bouillon" (manufactured by Wyler Foods, Division of Borden, Inc., Chicago, Illinois, U.S.A.):

(Ingredients: Salt, hydrolyzed vegetable protein, malto dextrin, sugar beef fat, water, monosodium glutamate, flavorings, corn sugar, beef extract, caramel color, hydrogenated vegetable fat and U.S. certified food color) at the rate of 0.1 ppm. The resulting beef flavored broth has an excellent vegetable-like, roasted meat-like, hydrolyzed vegetable-like protein flavor with excellent roasted meaty nuances and hydrolyzed vegetable protein-like after taste.

What is claimed is:

1. The process for augmenting or enhancing the aroma or taste of a foodstuff comprising adding to said foodstuff from 0.0003 parts per million up to about 300 parts per million based on total composition of at least one dialkyl mercaptal of a methylthioalkanal defined according to the structure:

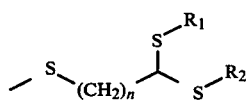

wherein n is an integer of from 1 to 3 and $R_1$ and $R_2$ are each the same or different and each represents $C_1$-$C_3$ lower alkyl.

2. The process of claim 1 wherein the dialkyl mercaptal of the methylthioalkanal defined according to the structure:

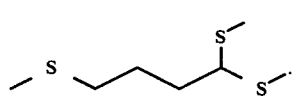

3. The process of claim 1 wherein the dialkyl mercaptal of the methylthioalkanal defined according to the structure:

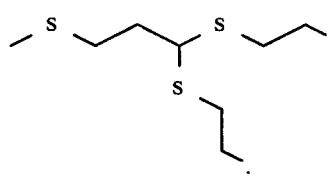

4. The process of claim 1 wherein the dialkyl mercaptal of the methylthioalkanal defined according to the structure:

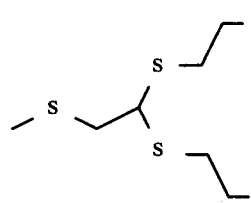

5. The process of claim 1 wherein the dialkyl mercaptal of the methylthioalkanal defined according to the structure:

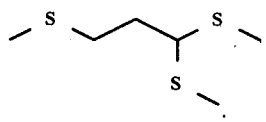

6. The process of claim 1 wherein the dialkyl mercaptal of the methylthioalkanal defined according to the structure:

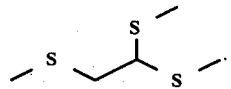

7. The process of claim 1 wherein the compound having the structure:

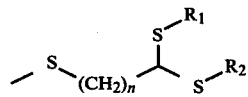

is a compound of the structure:

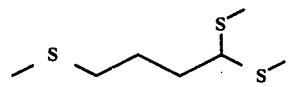

and intimately admixed therewith is at least one oxathiane defined according to a structure selected from the group consisting of:

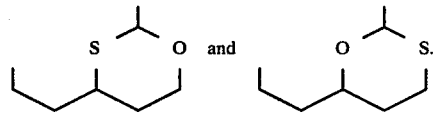

the mole ratio of compound having the structure:

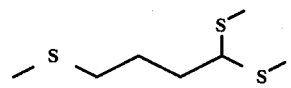

to oxathiane defined according to one of the structures:

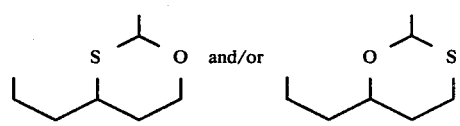

being from about 1:10 down to about 10:1.

* * * * *